(12) United States Patent
Sareen et al.

(10) Patent No.: US 10,221,395 B2
(45) Date of Patent: Mar. 5, 2019

(54) EFFICIENT METHOD FOR REPROGRAMMING BLOOD TO INDUCED PLURIPOTENT STEM CELLS

(71) Applicant: Cedars-Sinai Medical Center, Los Angeles, CA (US)

(72) Inventors: Dhruv Sareen, Porter Ranch, CA (US); Loren A. Ornelas, Los Angeles, CA (US); Clive Svendsen, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 15/184,241

(22) Filed: Jun. 16, 2016

(65) Prior Publication Data
US 2017/0362574 A1 Dec. 21, 2017

(51) Int. Cl.
C12N 5/00 (2006.01)
C12N 5/02 (2006.01)
C12N 5/074 (2010.01)

(52) U.S. Cl.
CPC ........ *C12N 5/0696* (2013.01); *C12N 2500/25* (2013.01); *C12N 2501/115* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2502/02* (2013.01); *C12N 2506/11* (2013.01); *C12N 2533/52* (2013.01)

(58) Field of Classification Search
CPC .............. C12N 5/0696; C12N 2500/25; C12N 2502/02; C12N 2533/52; C12N 2506/11; C12N 2501/60; C12N 2501/115; C12N 2501/602; C12N 2501/608; C12N 2501/606; C12N 2501/604; C12N 2501/603
See application file for complete search history.

(56) References Cited

U.S. PATENT DOCUMENTS

| | | | |
|---|---|---|---|
| 8,183,038 B2 | 5/2012 | Thomson et al. | |
| 8,257,941 B2 | 9/2012 | Sakurada et al. | |
| 8,268,620 B2 | 9/2012 | Thomson et al. | |
| 8,440,461 B2 | 5/2013 | Thomson et al. | |
| 8,546,140 B2 | 10/2013 | Mack et al. | |
| 8,691,574 B2 * | 4/2014 | Mack | C12N 5/0696 435/375 |
| 8,741,648 B2 | 6/2014 | Rajesh et al. | |
| 8,765,470 B2 | 7/2014 | Thomson et al. | |
| 9,328,332 B2 | 5/2016 | Mack | |
| 9,447,382 B2 | 9/2016 | Mack | |
| 9,499,786 B2 | 11/2016 | Thomson et al. | |
| 2009/0203141 A1 | 8/2009 | Lin et al. | |
| 2011/0104125 A1 | 5/2011 | Yu | |
| 2011/0200568 A1 | 8/2011 | Ikeda et al. | |
| 2012/0009676 A1 | 1/2012 | Mack | |
| 2012/0196360 A1 | 8/2012 | Okita et al. | |
| 2012/0315697 A1 | 12/2012 | Pettit et al. | |
| 2013/0040302 A1 | 2/2013 | Burke et al. | |
| 2013/0189778 A1 | 7/2013 | Mack | |
| 2013/0217117 A1 | 8/2013 | Thomson et al. | |
| 2014/0057355 A1 | 2/2014 | Thomson et al. | |
| 2014/0134143 A1 | 5/2014 | Baylink et al. | |
| 2014/0315306 A1 | 10/2014 | Tryggvason et al. | |
| 2015/0175973 A1 * | 6/2015 | Yamanaka | C12N 5/0696 435/455 |
| 2015/0297794 A1 | 10/2015 | Yamashita et al. | |
| 2016/0108369 A1 | 4/2016 | Kuno et al. | |
| 2016/0145642 A1 | 5/2016 | Cui et al. | |
| 2017/0107498 A1 | 4/2017 | Sareen et al. | |

FOREIGN PATENT DOCUMENTS

| | | |
|---|---|---|
| EP | 3152295 A1 | 4/2017 |
| WO | 2011016588 A1 | 2/2011 |
| WO | 2011056971 A2 | 5/2011 |
| WO | 2011138786 A2 | 11/2011 |
| WO | 2011/159684 A3 | 12/2011 |
| WO | 2013009825 A1 | 1/2013 |
| WO | 2013040445 A1 | 3/2013 |

(Continued)

OTHER PUBLICATIONS

Gibco (2011, Gibco catalog, Cat Nos. A141129-01,A14130-01, pp. 1-4.*
Chou (2011, Cell Res, 21:518-529).*
Okita (2013, Stem Cells, 31:458-466).*
Lu (2014, Biomaterial, 35:2816-2826).*
Stemcell Technologies, (Catalog 2013, TeSR TM-E7TM; . pdf-attached, https://www.stemcell.com/media/files/brochure/BR28069-TeSRE7_Reprogramming_Medium_Human_iPS_Cell_Induction.pdf).*
Bayart (2013 Curr Gene Therapy, 13:73-92).*

(Continued)

*Primary Examiner* — Valarie E Bertoglio
(74) *Attorney, Agent, or Firm* — Stephen W. Chen; Nixon Peabody LLP

(57) ABSTRACT

Described herein are methods and compositions related to generation of induced pluripotent stem cells (iPSCs). Improved techniques for establishing highly efficient, reproducible reprogramming using non-integrating episomal plasmid vectors. Using the described reprogramming protocol, one is able to consistently reprogram non-T cells with close to 100% success from non-T cell or non-B cell sources. Further advantages include use of a defined reprogramming media E7 and using defined clinically compatible substrate recombinant human L-521. Generation of iPSCs from these blood cell sources allows for recapitulation of the entire genomic repertoire, preservation of genomic fidelity and enhanced genomic stability.

21 Claims, 21 Drawing Sheets

Specification includes a Sequence Listing.

(56) References Cited

FOREIGN PATENT DOCUMENTS

| WO | 2013062140 A1 | 5/2013 |
| WO | 2015006725 A2 | 1/2015 |
| WO | 2015188131 A1 | 12/2015 |
| WO | 2017219000 A1 | 12/2017 |

OTHER PUBLICATIONS

International Search Report and Written Opinion for PCT/US2014/046405 dated Nov. 14, 2014, 7 pages.
International Preliminary Report on Patentability for PCT/US2014/046405 dated Jan. 12, 2016, 6 pages.
International Search Report and Written Opinion for PCT/US2015/034532 dated Sep. 15, 2015, 9 pages.
International Preliminary Report on Patentability for PCT/US2015/034532 dated Dec. 6, 2016, 7 pages.
Okita et al., A More Efficient Method to Generate Integration-Free Human iPS Cells, Nature Methods, 2011, vol. 8, pp. 409-412.
Rajesh et al., Human Lymphoblastoid B-cell Lines Reprogrammed to EBV-Free Induced Pluripotent Stem Cells, Blood, 2011, vol. 118(7), pp. 1797-1800.
Extended European Search Report for EP 15802756.5 dated Sep. 13, 2017, 9 pages.
Barrett et al., Reliable Generation of Induced Pluripotent Stem Cells from Human Lymphoblastoid Cell Lines: Reliable iPSC Generation from LCLs, Stem Cells Translational Medicine: SCTM, 2014, vol. 3(12), pp. 1429-1434.
Choi et al., Reprogramming of EBV-Immortalized B-Lymphocyte Cell Lines into Induced Pluripotent Stem Cells, Blood, 2011, vol. 118(7), pp. 1801-1805.
Ye et al., Hematopoietic Cells as Sources for Patient-Specific iPSCs and Disease Modelling, Cell Cycle, 2011, vol. 10(17), pp. 2840-2844.
International Search Report and Written Opinion for PCT/US2017/038041 dated Sep. 6, 2017, 9 pages.

* cited by examiner

Figure 1.
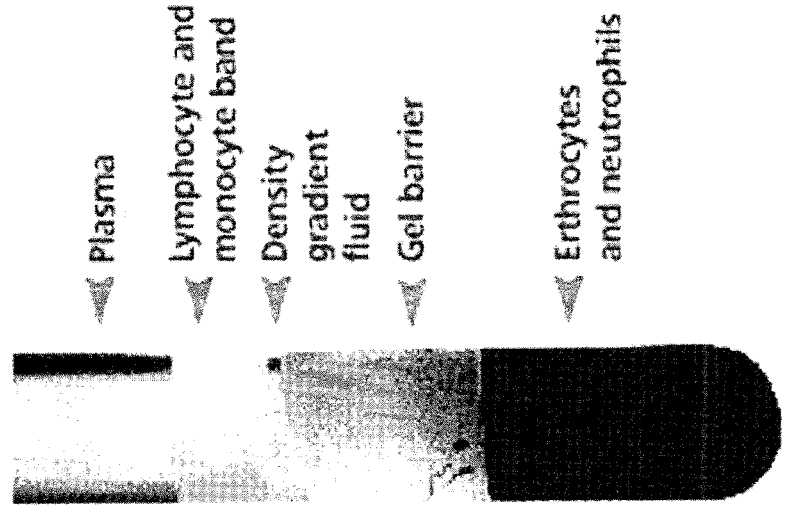
*Figure 1A.*
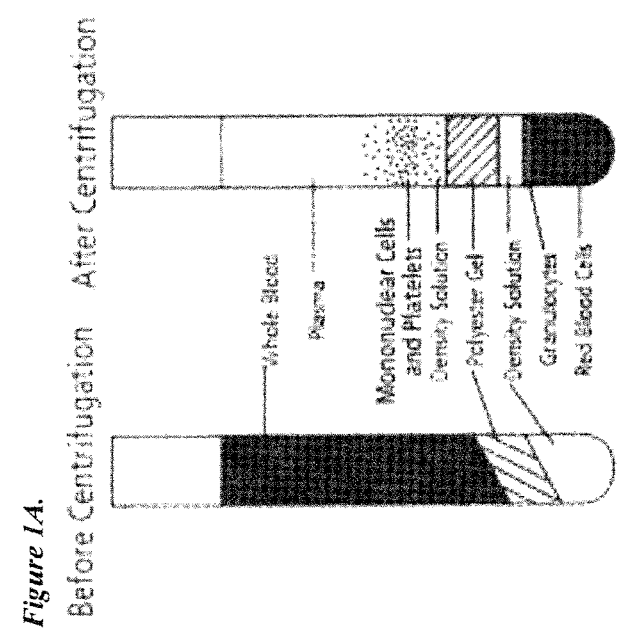
*Figure 1B.*

Figure 2.
*Figure 2A.*
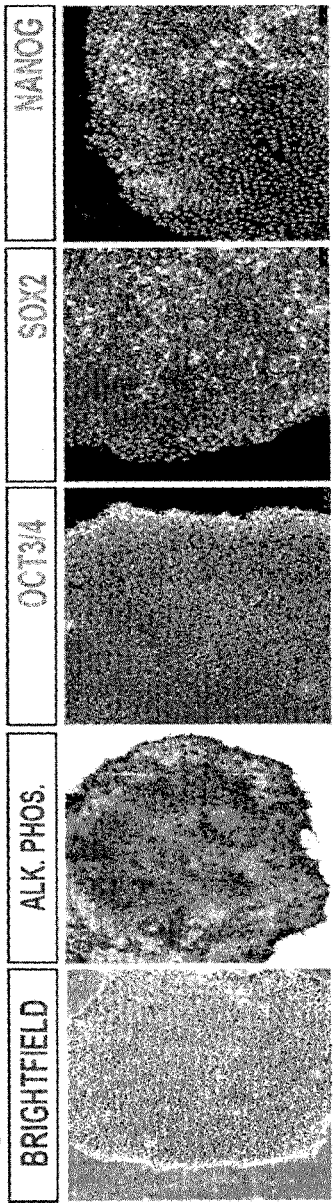
*Figure 2B.*
*Figure 2C.*
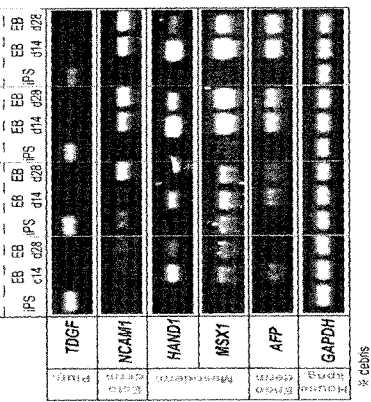
*Figure 2D.*
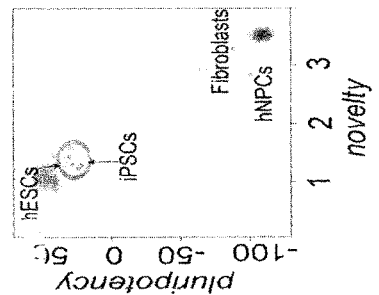

Figure 8.
*Figure 8A.*
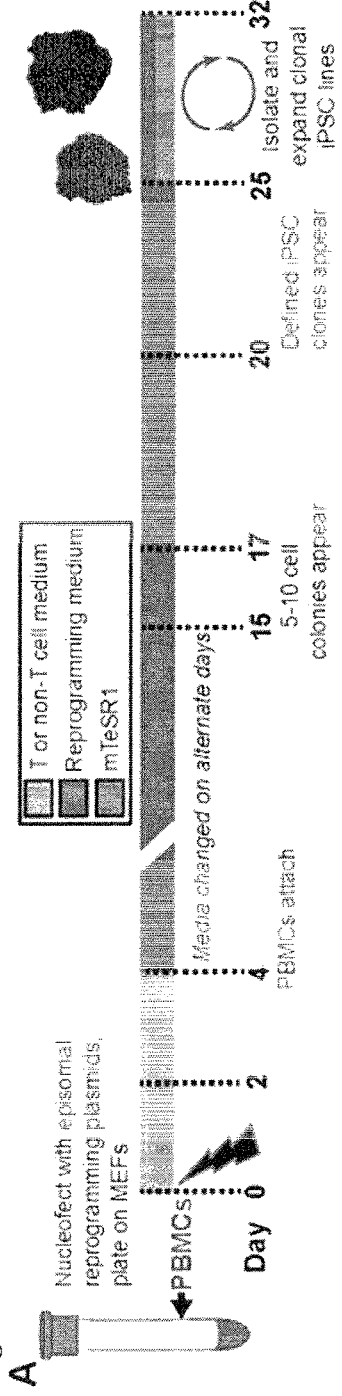
*Figure 8B.*
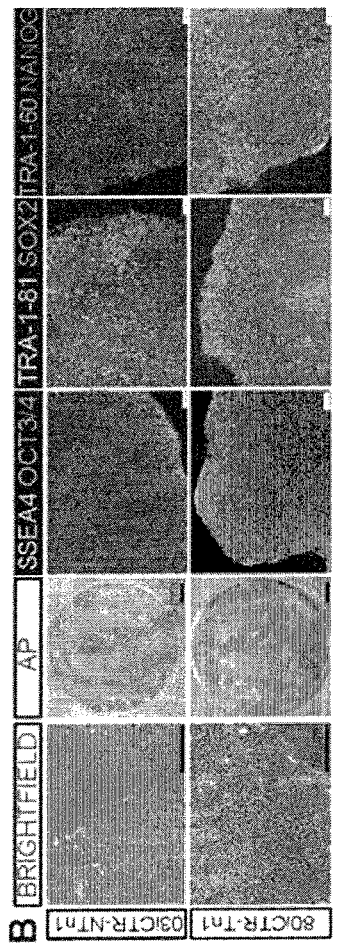
*Figure 8C.*
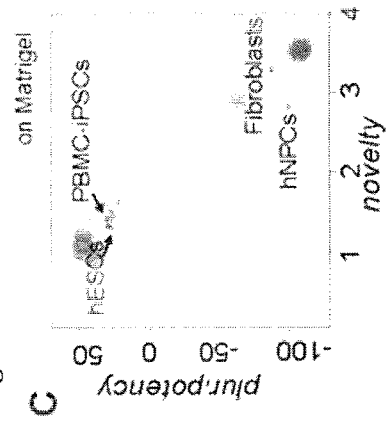

Figure 8.
*Figure 8D.*
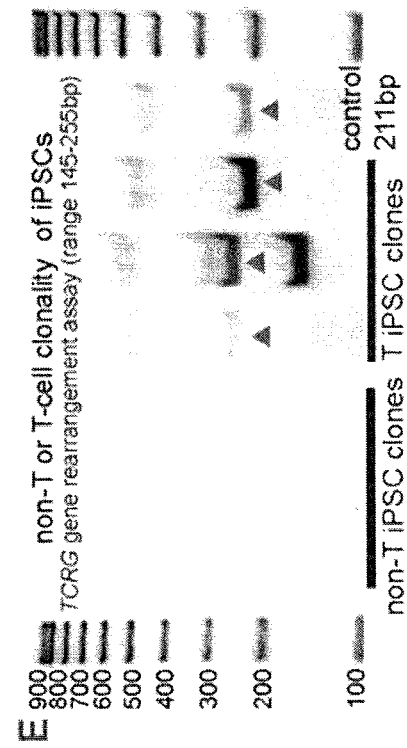
*Figure 8E.*
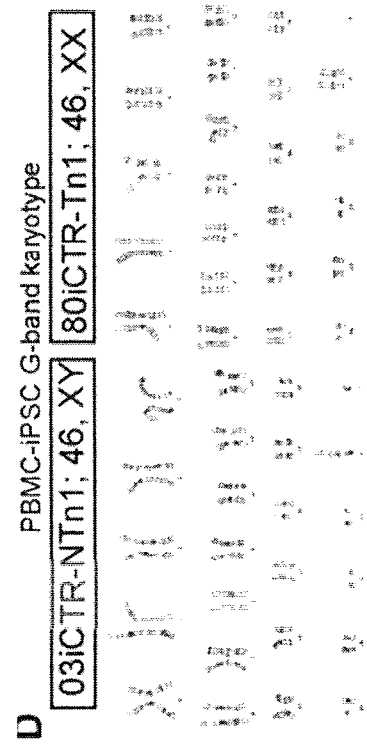

Figure 8.
*Figure 8F.*
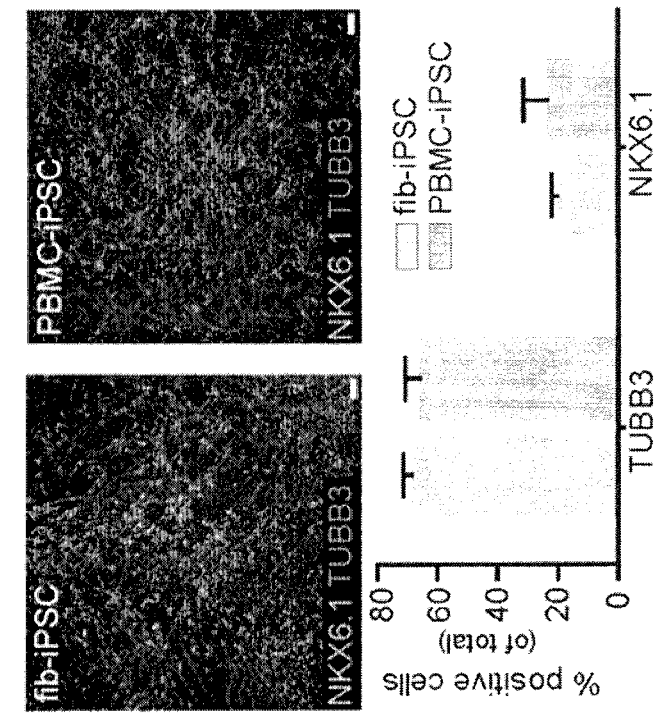
*Figure 8G.*
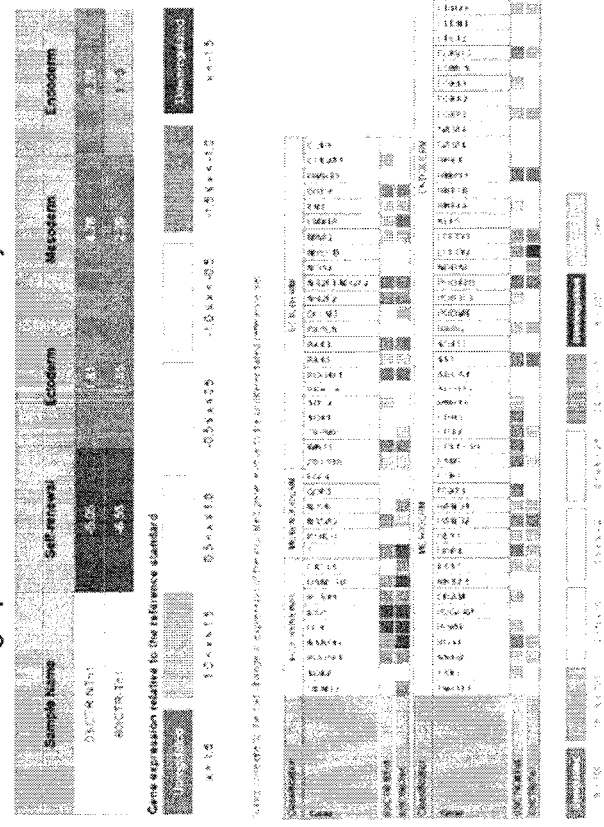

Figure 9.
*Figure 9A.*
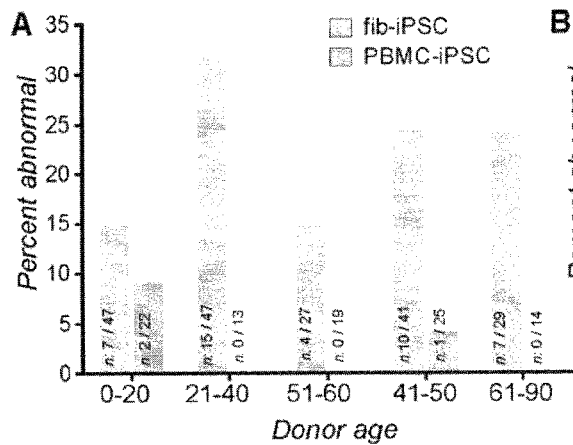
*Figure 9B.*
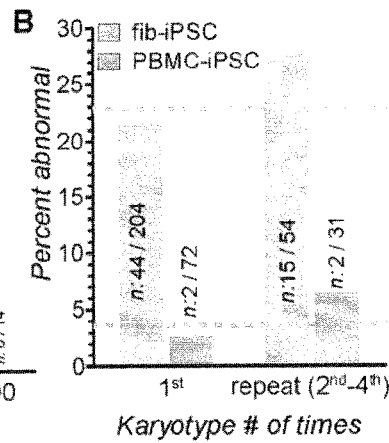
*Figure 9C.*
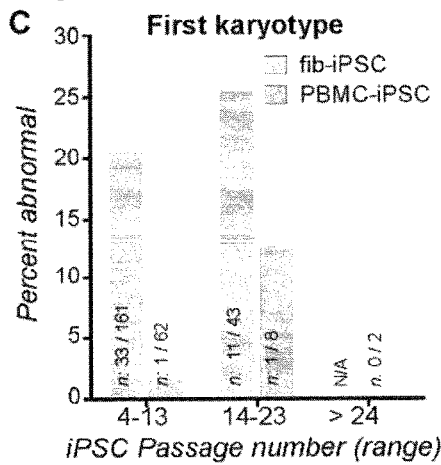
*Figure 9D.*
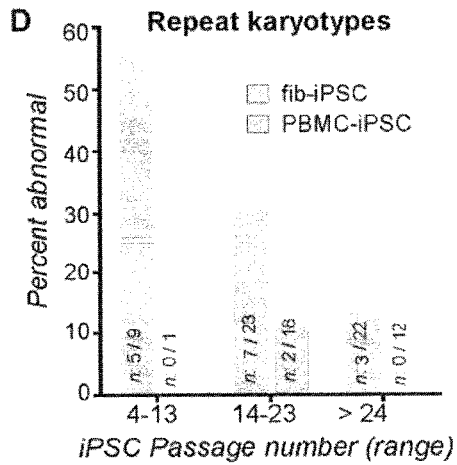

Figure 10.
*Figure 10A.*
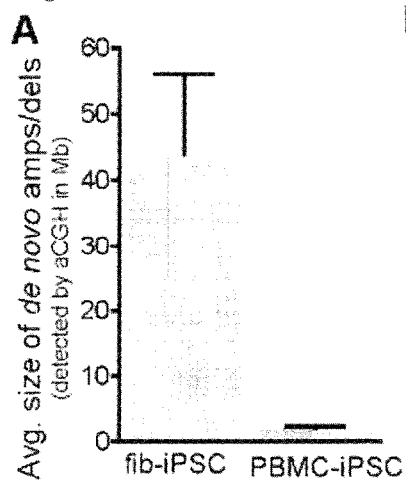
*Figure 10B.*
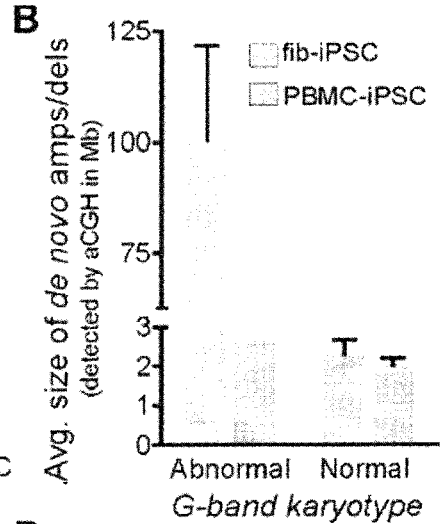
*Figure 10C.*
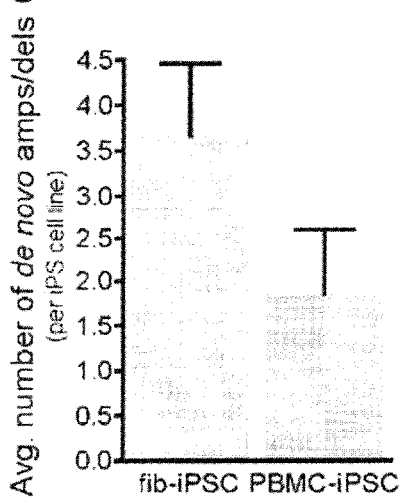
*Figure 10D.*
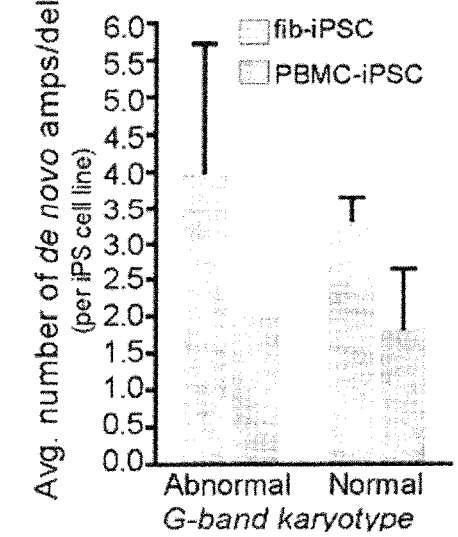

| Chr. | Amp/Del | Start-stop (bp) | Size (Mb) | Chr. Band | Genes |
|---|---|---|---|---|---|
| 7 | Amp | 121,471,771-122,676,877 | 1.2-1.5 | q31.32 | PTPRZ1, AASS, CADPS2, TAS2R16, FEZF1 |
| 10 | Del | 3,335,606-4,720,135 | 1.2-1.4 | q15.2-q15.1 | LOC154860, RNF133, RNF148, KLF6, LOC100216001, LOC338588 |
| 16 | Del | 32,624,578-33,604,468 | 0.8-1.0 | p11.2 | TP53TG3, TP53TG3B, LOC653550, SLC6A10P, LOC390705 |
| 21 | Del | 9,832,936-10,944,060 | 1.1 | p11.2-p11.1 | TPTE, LOC100132288 |

SEQUENCE LISTING

<160> NUMBER OF SEQ ID NOS: 48

<210> SEQ ID NO 1
<211> LENGTH: 23
<212> TYPE: DNA
<213> ORGANISM: Homo sapiens

<400> SEQUENCE: 1
ccccagggcc ccattttggt acc                                   23

<210> SEQ ID NO 2
<211> LENGTH: 26

```
<212> TYPE: DNA
<213> ORGANISM: Homo sapiens

<400> SEQUENCE: 2
acctcagttt gaatgcatgg gagagc                                     26

<210> SEQ ID NO 3
<211> LENGTH: 20
<212> TYPE: DNA
<213> ORGANISM: Homo sapiens

<400> SEQUENCE: 3
cattcaaact gaggtaaggg                                            20

<210> SEQ ID NO 4
<211> LENGTH: 22
<212> TYPE: DNA
<213> ORGANISM: Homo sapiens

<400> SEQUENCE: 4
tagcgtaaaa ggagcaacat ag                                         22

<210> SEQ ID NO 5
<211> LENGTH: 24
<212> TYPE: DNA
<213> ORGANISM: Homo sapiens

<400> SEQUENCE: 5
ttcacatgtc ccagcactac caga                                       24

<210> SEQ ID NO 6
<211> LENGTH: 26
<212> TYPE: DNA
<213> ORGANISM: Homo sapiens

<400> SEQUENCE: 6
tcacatgtgt gagaggggca gtgtgc                                     26

<210> SEQ ID NO 7
<211> LENGTH: 24
<212> TYPE: DNA
<213> ORGANISM: Homo sapiens

<400> SEQUENCE: 7
ttcacatgtc ccagcactac caga                                       24

<210> SEQ ID NO 8
<211> LENGTH: 22
<212> TYPE: DNA
<213> ORGANISM: Homo sapiens

<400> SEQUENCE: 8
tttgtttgac aggagcgaca at                                         22

<210> SEQ ID NO 9
<211> LENGTH: 24
<212> TYPE: DNA
<213> ORGANISM: Homo sapiens

<400> SEQUENCE: 9
acccatcctt cctgcccgat caga                                       24

<210> SEQ ID NO 10
```

```
<211> LENGTH: 24
<212> TYPE: DNA
<213> ORGANISM: Homo sapiens

<400> SEQUENCE: 10
ttggtaatgg agcggcggga cttg                                          24

<210> SEQ ID NO 11
<211> LENGTH: 23
<212> TYPE: DNA
<213> ORGANISM: Homo sapiens

<400> SEQUENCE: 11
ccacctcgcc ttacacatga aga                                           23

<210> SEQ ID NO 12
<211> LENGTH: 22
<212> TYPE: DNA
<213> ORGANISM: Homo sapiens

<400> SEQUENCE: 12
tagcgtaaaa ggagcaacat ag                                            22

<210> SEQ ID NO 13
<211> LENGTH: 26
<212> TYPE: DNA
<213> ORGANISM: Homo sapiens

<400> SEQUENCE: 13
gcgaacccaa gacccaggcc tgctcc                                        26

<210> SEQ ID NO 14
<211> LENGTH: 25
<212> TYPE: DNA
<213> ORGANISM: Homo sapiens

<400> SEQUENCE: 14 caggggtct gctcgcaccg tgatg                                          25

<210> SEQ ID NO 15
<211> LENGTH: 21
<212> TYPE: DNA
<213> ORGANISM: Homo sapiens

<400> SEQUENCE: 15
ggctgagaag aggatggcta c                                             21

<210> SEQ ID NO 16
<211> LENGTH: 22
<212> TYPE: DNA
<213> ORGANISM: Homo sapiens

<400> SEQUENCE: 16
tttgtttgac aggagcgaca at                                            22

<210> SEQ ID NO 17
<211> LENGTH: 25
<212> TYPE: DNA
<213> ORGANISM: Homo sapiens

<400> SEQUENCE: 17
agccatatgg tagcctcatg tccgc                                         25
```

-continued

```
<210> SEQ ID NO 18
<211> LENGTH: 30
<212> TYPE: DNA
<213> ORGANISM: Homo sapiens

<400> SEQUENCE: 18
tcaattctgt gcctccggga gcagggtagg                              30

<210> SEQ ID NO 19
<211> LENGTH: 25
<212> TYPE: DNA
<213> ORGANISM: Homo sapiens

<400> SEQUENCE: 19
agccatatgg tagcctcatg tccgc                                   25

<210> SEQ ID NO 20
<211> LENGTH: 22
<212> TYPE: DNA
<213> ORGANISM: Homo sapiens

<400> SEQUENCE: 20
tagcgtaaaa ggagcaacat ag                                      22

<210> SEQ ID NO 21
<211> LENGTH: 21
<212> TYPE: DNA
<213> ORGANISM: Homo sapiens

<400> SEQUENCE: 21
cctggaggag aagaggaaag a                                       21

<210> SEQ ID NO 22
<211> LENGTH: 21
<212> TYPE: DNA
<213> ORGANISM: Homo sapiens

<400> SEQUENCE: 22
ttgaggacct ctgtgtattt g                                       21

<210> SEQ ID NO 23
<211> LENGTH: 21
<212> TYPE: DNA
<213> ORGANISM: Homo sapiens

<400> SEQUENCE: 23
tgctgtctcc atgtttgatg t                                       21

<210> SEQ ID NO 24
<211> LENGTH: 21
<212> TYPE: DNA
<213> ORGANISM: Homo sapiens

<400> SEQUENCE: 24
tctctgctcc ccacctctaa g                                       21

<210> SEQ ID NO 25
<211> LENGTH: 21
<212> TYPE: DNA
<213> ORGANISM: Homo sapiens

<400> SEQUENCE: 25
atcagggcca agacatagag a                                       21
```

```
<210> SEQ ID NO 26
<211> LENGTH: 20
<212> TYPE: DNA
<213> ORGANISM: Homo sapiens

<400> SEQUENCE: 26
gccaatgcaa cttggacgtt                                              20

<210> SEQ ID NO 27
<211> LENGTH: 24
<212> TYPE: DNA
<213> ORGANISM: Homo sapiens

<400> SEQUENCE: 27
catagaagaa gaagaggatg aaga                                         24

<210> SEQ ID NO 28
<211> LENGTH: 24
<212> TYPE: DNA
<213> ORGANISM: Homo sapiens

<400> SEQUENCE: 28
gtagggattc gagggaatta ctga                                         24

<210> SEQ ID NO 29
<211> LENGTH: 19
<212> TYPE: DNA
<213> ORGANISM: Homo sapiens

<400> SEQUENCE: 29
atggaacacg accttgaga                                               19

<210> SEQ ID NO 30
<211> LENGTH: 20
<212> TYPE: DNA
<213> ORGANISM: Homo sapiens

<400> SEQUENCE: 30
tgagcaggat gaggtctagg                                              20

<210> SEQ ID NO 31
<211> LENGTH: 20
<212> TYPE: DNA
<213> ORGANISM: Homo sapiens

<400> SEQUENCE: 31
cacctcaacc tggagacaat                                              20

<210> SEQ ID NO 32
<211> LENGTH: 20
<212> TYPE: DNA
<213> ORGANISM: Homo sapiens

<400> SEQUENCE: 32
tgaagcaggc gtggtttcaa                                              20

<210> SEQ ID NO 33
<211> LENGTH: 20
<212> TYPE: DNA
<213> ORGANISM: Homo sapiens

<400> SEQUENCE: 33
tcgggggtgt tagagacaac                                              20
```

```
<210> SEQ ID NO 34
<211> LENGTH: 20
<212> TYPE: DNA
<213> ORGANISM: Homo sapiens

<400> SEQUENCE: 34
ttccacgagg gtagtgaacc                                        20

<210> SEQ ID NO 35
<211> LENGTH: 20
<212> TYPE: DNA
<213> ORGANISM: Homo sapiens

<400> SEQUENCE: 35
accacagtcc atgccatcac                                        20

<210> SEQ ID NO 36
<211> LENGTH: 20
<212> TYPE: DNA
<213> ORGANISM: Homo sapiens

<400> SEQUENCE: 36
tccaccaccc tgttgctgta                                        20

<210> SEQ ID NO 37
<211> LENGTH: 20
<212> TYPE: DNA
<213> ORGANISM: Homo sapiens

<400> SEQUENCE: 37
tccttctacg gacggaactg                                        20

<210> SEQ ID NO 38
<211> LENGTH: 20
<212> TYPE: DNA
<213> ORGANISM: Homo sapiens

<400> SEQUENCE: 38
agaaatgcct gaggaaagca                                        20

<210> SEQ ID NO 39
<211> LENGTH: 20
<212> TYPE: DNA
<213> ORGANISM: Homo sapiens

<400> SEQUENCE: 39
gattcctcct ccaccctcac                                        20

<210> SEQ ID NO 40
<211> LENGTH: 23
<212> TYPE: DNA
<213> ORGANISM: Homo sapiens

<400> SEQUENCE: 40
caatattctg cctggcctgg atg                                    23

<210> SEQ ID NO 41
<211> LENGTH: 21
<212> TYPE: DNA
<213> ORGANISM: Homo sapiens

<400> SEQUENCE: 41
```
ccacacccac tcagagccat t                                           21

<210> SEQ ID NO 42
<211> LENGTH: 20
<212> TYPE: DNA
<213> ORGANISM: Homo sapiens

<400> SEQUENCE: 42
caccccacca ccaaaacctt                                             20

<210> SEQ ID NO 43
<211> LENGTH: 24
<212> TYPE: DNA
<213> ORGANISM: Homo sapiens

<400> SEQUENCE: 43
cgagaggacc ccgtggatgc agag                                        24

<210> SEQ ID NO 44
<211> LENGTH: 24
<212> TYPE: DNA
<213> ORGANISM: Homo sapiens

<400> SEQUENCE: 44
ggcggccatc ttcagcttct ccag                                        24

<210> SEQ ID NO 45
<211> LENGTH: 28
<212> TYPE: DNA
<213> ORGANISM: Homo sapiens

<400> SEQUENCE: 45
gaatgctgca aactgaccac gctggaac                                    28

<210> SEQ ID NO 46
<211> LENGTH: 28
<212> TYPE: DNA
<213> ORGANISM: Homo sapiens

<400> SEQUENCE: 46
tggcattcaa gagggttttc agtctgga                                    28

<210> SEQ ID NO 47
<211> LENGTH: 18
<212> TYPE: DNA
<213> ORGANISM: Homo sapiens

<400> SEQUENCE: 47
ctatcatgct ggctgcct                                               18

<210> SEQ ID NO 48
<211> LENGTH: 20
<212> TYPE: DNA
<213> ORGANISM: Homo sapiens

<400> SEQUENCE: 48
ctacaacacc cttctcacag                                             20

EFFICIENT METHOD FOR REPROGRAMMING BLOOD TO INDUCED PLURIPOTENT STEM CELLS

FIELD OF INVENTION

Described herein are methods and compositions related to regenerative medicine including the derivation of induced pluripotent stem cells (iPSCs) from whole blood and peripheral blood, such methods and compositions that provide a renewable source of transplant material.

BACKGROUND

Pluripotent stem cells ("pSCs") present broad opportunities to generate therapeutic materials for use in regenerative medicine, as well as providing invaluable in vitro models for studying disease initiation and progression. One category of pSCs, induced pluripotent stem cells ("iPSCs"), possess the hallmark stem cell properties of self-renewal (i.e., immortal) and differentiation capacity into cells derived from all three embryonic germ layers (i.e., pluripotency). These cells can be obtained through "reprogramming", which involves dedifferentiation of cells from non-embryonic sources, such as adult somatic cells. The reprogramming process obviates potential ethical concerns over embryonic source material for other types such pSCs, such as embryonic stem cells ("ESCs"), while providing a further benefit of enabling potential patient-specific immunological incompatibility.

In addition to establishing robust reprogramming techniques, full realization of therapeutic goals for stem-cell regenerative medicine further requires consideration of the types of host cells that can serve as a resource for renewable regenerative material. Ideally, cells would possess not only the requisite plasticity for successful reprogramming and stability in subsequent propagation, but also provide advantages in clinical aspects, such as ease of isolation, storage, stability and maintenance. In this regard, blood cells represent an attractive choice for such uses, given their wide use medical diagnostics and as a highly accessible resource for cellular reprogramming. Whereas fibroblasts have been a widely used cellular source for many reprogramming experiments performed in the last decade, this source material but may not be the best choice for directed reprogramming. Skin biopsy to obtain fibroblasts is an invasive, non-sterile procedure requiring expansion of harvested cells before experimentation. Most importantly, skin cells harbor more mutations due to environmental insults such as UV irradiation than cells from inside the body such as blood.

Given the eventual therapeutic goal of generating patient-specific, immunocompatible biological material, there is a great need in the art to establish a robust and reproducible means for reprogramming cells, along with identifying sources of therapeutic materials suitable for eventual clinical application. Such improved methods would need to possess high efficiency of reprogramming, consistent reproduction, produce cells possessing genomic stability and be readily extendible to a variety of cell types.

Described herein are improved techniques for establishing highly efficient, reproducible reprogramming using non-integrating episomal plasmid vectors, including generation of iPSCs from non-T cell, non-B cell component in blood samples. These described approaches allow for use of blood as a readily accessible resource for cellular reprogramming with superior properties in genomic and karyotype stability.

SUMMARY OF THE INVENTION

Described herein is a method of generating blood cell derived induced pluripotent stem cells, comprising providing a quantity of blood cells, delivering a quantity of reprogramming factors into the blood cells, and culturing the blood cells in a reprogramming media for at least 4 days, wherein delivering the reprogramming factors, and culturing in a reprogramming media generates blood cell derived induced pluripotent stem cells. In other embodiments, delivering a quantity of reprogramming factors comprises nucleofection. In other embodiments, the reprogramming factors comprise one or more factors selected from the group consisting of: Oct-4, Sox-2, Klf-4, c-Myc, Lin-28, SV40 Large T Antigen ("SV40LT"), and short hairpin RNAs targeting p53 ("shRNA-p53"). In other embodiments, the reprogramming factors are encoded in one or more oriP/EBNA1 derived vectors. In other embodiments, the one or more oriP/EBNA1 derived vectors comprise pEP4 E02S ET2K, pCXLE-hOCT3/4-shp53-F, pCXLE-hSK, pCXLE-hUL, and pCXWB-EBNA1. In other embodiments, plating of the blood cells on a treated cell culture surface after delivering reprogramming factors into the blood cells, and culturing the blood cells in a reprogramming media on said treated cell culture surface. In other embodiments, the treated cell culture surface comprises plating of mouse embryonic feeders (MEFs). In other embodiments, the treated cell culture surface comprises an extracellular matrix protein. In other embodiments, the extracellular matrix protein comprises laminin. In other embodiments, laminin comprises L-521. In other embodiments, the reprogramming media comprises embryonic stem cell (ESC) media. In other embodiments, the ESC media comprises basic fibroblast growth factor (bFGF). In other embodiments, the reprogramming media comprises E7 media. In other embodiments, the reprogramming media comprises E7 media comprising L-Ascorbic Acid, Transferrin, Sodium Bicarbonate, Insulin, Sodium Selenite and/or bFGF. In other embodiments, culturing the blood cells in a reprogramming media is for at least 4, 5, 6, 7, 8, 9, 10, 11, 12, 13, 14, 15, or 16 days. In other embodiments, culturing the blood cells in a reprogramming media is for at least 17, 18, 19, 20, 21, 22, 23, 24, 25, 26, 27, 28, 29, 30 or 31 days. Further described herein is a cell line comprising blood cell derived induced pluripotent stem cells generated by the aforementioned method. In other embodiments, the blood cells are isolated from a subject possessing a disease mutation. In other embodiments, the disease mutation is associated with a neurodegenerative disease, disorder and/or condition. In other embodiments, the disease mutation is associated with an inflammatory bowel disease, disorder, and/or condition. In other embodiments, the blood cells are non T-cell, non B-cell mononuclear cells. In other embodiments, the blood cells are a sample drawn from a human subject. In other embodiments, the sample is whole blood. In other embodiments, the sample is peripheral blood. In other embodiments, the sample comprises an isolated component of non T-cell, non B-cell mononuclear cells. Further described herein is a blood cell derived induced pluripotent stem cell line.

Further described herein is a method for generating induced pluripotent stem cells, comprising providing a quantity of blood cells, delivering a quantity of reprogramming factors into the blood cells, plating the blood cells on a treated cell culture surface and culturing the blood cells in a reprogramming media for at least 4 days, wherein delivering the reprogramming factors, and culturing in a reprogramming media generates blood cell derived induced pluripotent stem cells. In other embodiments, delivering a quantity of reprogramming factors comprises nucleofection, the reprogramming factors comprise one or more factors selected from the group consisting of: Oct-4, Sox-2, Klf-4, c-Myc, Lin-28, SV40 Large T Antigen ("SV40LT"), and short hairpin RNAs targeting p53 ("shRNA-p53"), encoded in one or more oriP/EBNA1 derived vectors. In other embodiments, the one or more oriP/EBNA1 derived vectors comprise pEP4 E02S ET2K, pCXLE-hOCT3/4-shp53-F, pCXLE-hSK, pCXLE-hUL, and pCXWB-EBNA1. In other embodiments, the treated cell culture surface comprises plating of mouse embryonic feeders (MEFs). In other embodiments, the treated cell culture surface comprises an extracellular matrix protein. In other embodiments, the extracellular matrix protein comprises laminin. In other embodiments, laminin comprises L-521. In other embodiments, the reprogramming media comprises embryonic stem cell (ESC) media comprising basic fibroblast growth factor (bFGF). In other embodiments, the reprogramming media comprises E7 media comprising L-Ascorbic Acid, Transferrin, Sodium Bicarbonate, Insulin, Sodium Selenite and/or bFGF. In other embodiments, culturing the blood cells in a reprogramming media is for at least 4, 5, 6, 7, 8, 9, 10, 11, 12, 13, 14, 15, or 16 days. In other embodiments, culturing the blood cells in a reprogramming media is for at least 17, 18, 19, 20, 21, 22, 23, 24, 25, 26, 27, 28, 29, 30 or 31 days. In other embodiments, the blood cells are a sample drawn from a human subject. In other embodiments, the sample is whole blood. In other embodiments, the sample is peripheral blood. In other embodiments, the sample comprises an isolated component of non T-cell, non B-cell mononuclear cells. Further described herein is a blood cell derived induced pluripotent stem cell line.

BRIEF DESCRIPTION OF FIGURES

FIG. 1(A) to FIG. 1(B). Separation of Blood Components. FIG. 1(A) Schematic showing separated components. FIG. 1(B) Picture of separated components.

FIG. 2(A) to FIG. 2(E). Quality Control: iPS cells. Various measures of quality control for generated cells are shown including FIG. 2(A) microscopy, and staining for pluripotent stem cell markers. FIG. 2(B) Depiction of the pluripotency of stem cells. FIG. 2(C) Karyotype analysis. FIG. 2(D) RT-PCR of pluripotent and lineage specific markers for different cell lines. FIG. 2(E) Pluripotent stem cells as capable of differentiating into all three embryonic lineages.

(FIG. 6(A)) fib-iPSCs (n: 59) of total 258 fib-iPSC cultures karyotyped, and (FIG. 6(B)) BC-iPSCs (n: 4) of total BC-iPSCss karyotyped (n: 106).

FIG. 7(A) Distribution of abnormal karyotypes in relation to passage number. FIG. 7(B) Distribution of abnormal karyotypes in relation to age of tissue donor Marooon, monosomy, loss of a whole chromosome;

FIG. 8(A) to 8(F). Reliable epsimoal reprogramming of PBMCs into iPSCs. FIG. 8(A): Schematic depicting the episomal reprogramming process and timeline of iPSC generation from PBMCs. FIG. 8(B): Bright-field images of the reprogrammed iPSC colonies from PBMCs obtained two healthy volunteers, one with a non-T cell (03iCTR-NTn1) reprogramming method and another with a T-cell (80iCTR-Tn1) reprogramming method, show a high nuclear-to-cytoplasmic ratio, are alkaline phosphatase positive and immunopositive for the surface antigens, SSEA4, TRA-1-60, TRA-1-81; and nuclear pluripotency markers OCT3/4, SOX2 and NANOG. Scale bar, 75 μm. FIG. 8(C): Microarray Illumina gene-chip and bioinformatics based PluriTest confirms pluripotency levels in the BC-iPSCs. (D): The PBMC-iPSC lines maintained a normal G-band karyotype as shown from the two representative lines. FIG. 8(E): non-T or T-cell clonality assay. FIG. 8(F): Quantitative RT-PCR analyses of POU5F1 (OCT4), SOX2, LIN28, L-MYC, and KLF4 expression in 49iCTR and 84iSMA LCL-iPSCs relative to H9 hESCs. (G) T cell receptor gene rearrangement assay shows different sets of PCR primers were used to detect TCRG gene rearrangements occurring in the BC-iPSCs derived from the T-cell method, while PCR products in the 145-255 bp range were not detectable in the non-T cell iPSC clones. A clonal positive control was included. FIG. 8(F): TaqMan hPSC Scorecard table showing the tri-lineage potential of the representative BC-iPSCs rom selected genes in four gene groups (self-renewal/pluripotency, ectoderm, endoderm, and mesoderm) comparing spontaneous in vitro EB differentiation of EBs derived from the PBMC-iPSC lines. FIG. 8(G): Directed neuronal differentiation of representative fibroblast-derived (n: 26) and PBMC-derived iPSCs (n: 12) showing equivalent numbers of ectodermal (Nkx6.1+/β₃-tubulin+ neuronal cells). Scale bar, 75 μm.

FIG. 9(A) to FIG. 9(D): Compared to fib-iPSC, the BC-iPSCs are more stable over extended culture. FIG. 9(A) Percent abnormal G-band karyotypes observed in the iPSC lines in correlation to donor age of fibroblasts and PBMCs. FIG. 9(B) Percent abnormal G-band karyotypes at the first karyotype post-reprogramming and in repeat karyotypes for iPSC lines evaluated in extended cell culture. The dotted lines represent the overall average karyotype abnormality rate for fib-iPSCs (orange) and BC-iPSCs (blue). FIG. 9(C) Percent abnormal at the first G-band karyotypes evaluated for the fib- and PBMC-iPSC clonal lines in relation to the passage number of the iPSCs. FIG. 9(D) Percent abnormal at the second-fourth (repeat) G-band karyotypes evaluated for the fib- and PBMC-iPSC clonal lines in relation to the passage number of the iPSCs.

FIG. 10(A) to FIG. 10(E): Comparative genomic hybridization confirms that the BC-iPSCs have relatively small and fewer submicroscopic cytogenetic aberrations compared to fib-iPSCs. (FIG. 10(A)-FIG. 10(B)) The average size of de novo acquired amplifications and deletions detected by aCGH in Mb of fib-iPSCs (n: 6) and PBMC-iPSCs (n:7) when compared to each iPSC line's parental cells. The iPSC lines used in aCGH had both abnormal and normal G-band karyotypes. Abnormal: fib-iPSC (n: 3) and PBMC-iPSC (n: 2). Normal: fib-iPSC (n: 3) and PBMC-iPSC (n: 5). (FIG. 10(C)-FIG. 10(D)) The average number of de novo acquired amplifications and deletions detected by aCGH in Mb of fib-iPSCs (n: 6) and PBMC-iPSCs (n: 7) when compared to each iPSC line's parental cells. FIG. 10(E) A list of most recurrent submicroscopic amps/dels observed in the fib- or PBMC-iPSC lines observed in our laboratory.

FIG. 11(A) Lack of plasmid-based EBNA gene expression using a assay in the genomic DNA of the BC-iPSCs. FIG. 11 (C) as well as plasmid-derived expression (Pla), which is undetectable in the iPSC lines.

(FIG. 12(A)) LCL-iPSCs (n: 15) of total 60 LCL-iPSC cultures karyotyped, and (FIG. 12(B)) epithelial-iPSCs (n: 7) of total BC-iPSCs karyotyped (n: 26).

DETAILED DESCRIPTION

Figures 2, 2E:
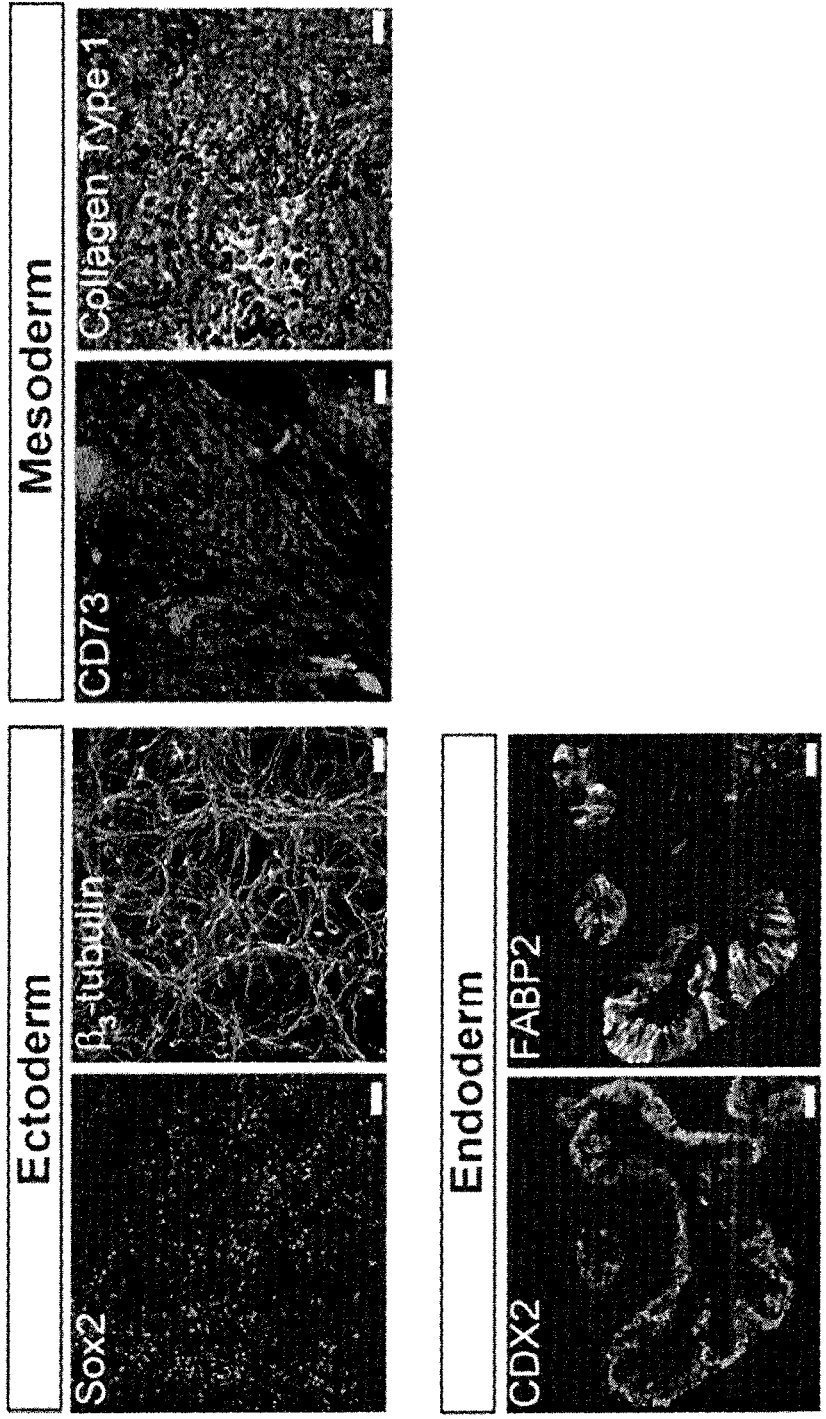
Figure 3:
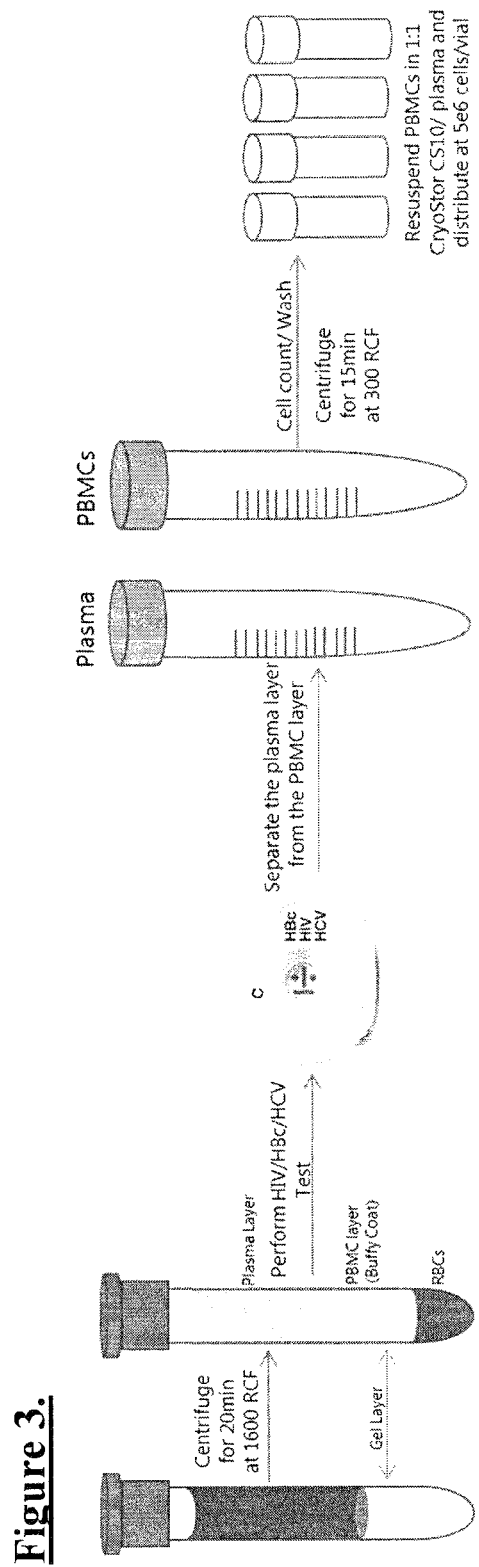
FIG. 3. PBMC isolation and cryopreservation process. Process for obtaining blood cells utilized as a source for reprogramming and generation of iPSCs.
Figure 4:
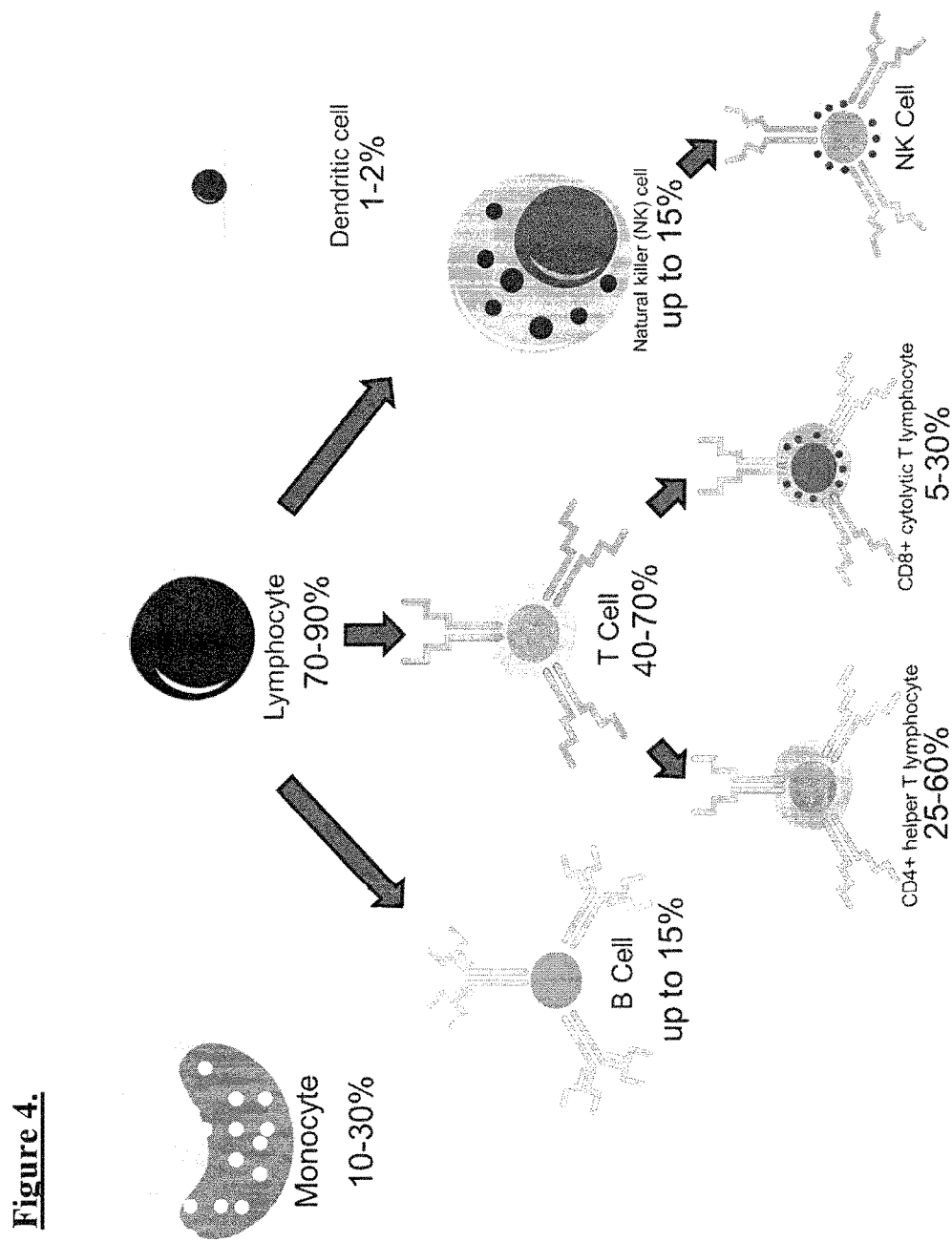
FIG. 4. Peripheral blood mononuclear cells (PBMCs). Depiction of the various components of blood, including populations of PBMCs and relative population abundance.
Figure 5:
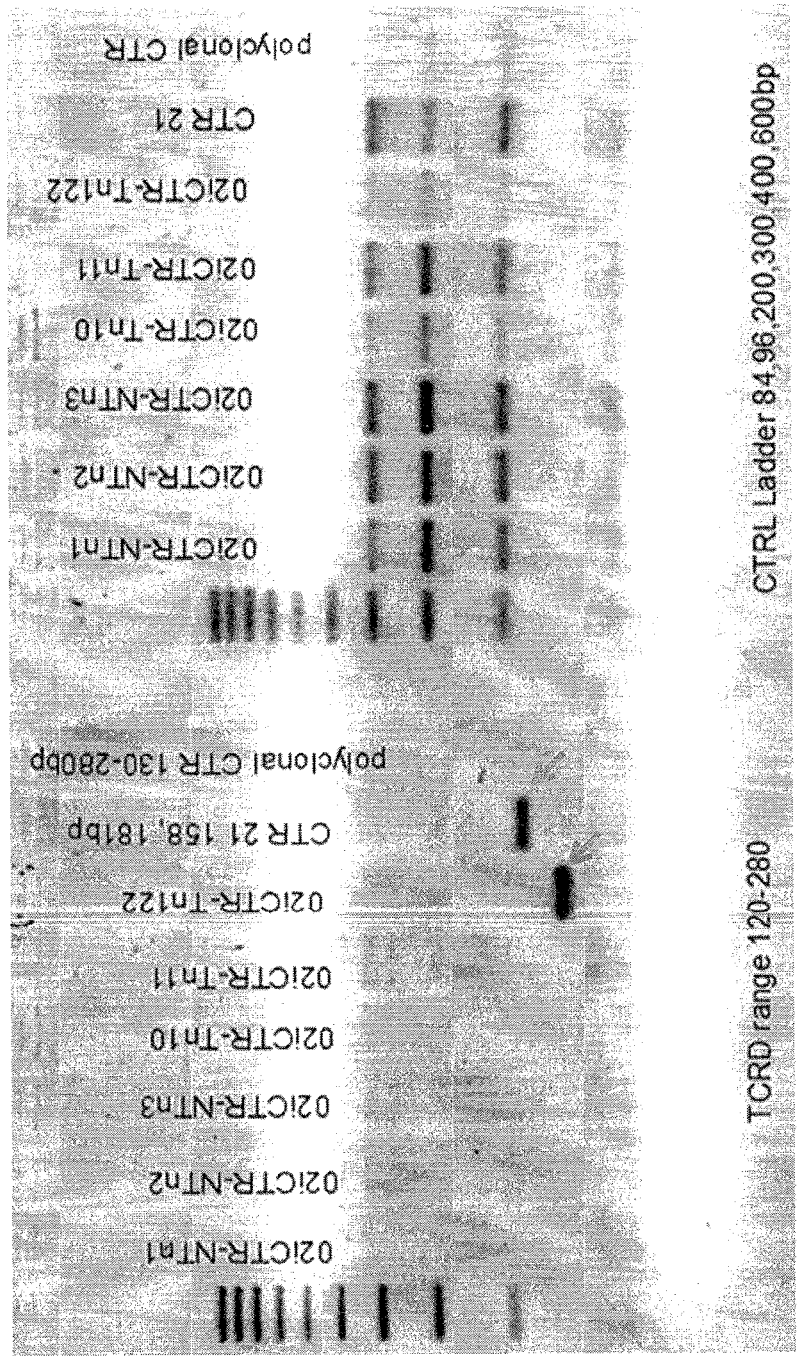
FIG. 5. T-cell Receptor Clonality Assay for iPSCs derived from Blood.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul., 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Patient-specific induced pluripotent stem cells ("iPSCs") hold great promise for many applications, including disease modeling to elucidate mechanisms involved in disease pathogenesis, drug screening, and ultimately regenerative medicine therapies. A frequently used starting source of cells for reprogramming has been dermal fibroblasts isolated from skin biopsies. However, as described, iPSCs derived from skin punch biopsies are more invasive, require a prolonged 2-3 week period of expansion in culture prior to reprogramming. Most importantly, there are greater numbers of mutations associated with epidermal exposure to UV light, raising concerns over the safety of the iPSCs cells derived from skin. Issues with the common fibroblast cell source would be circumvented with peripheral blood, which can be utilized as an easily accessible source of patient tissue for reprogramming. Peripheral blood is the most accessible adult tissue and permits access to numerous frozen samples already stored at blood banks. Additionally, many repositories have stored peripheral or lymphoblast blood with specific genotypes.

Maintaining genomic integrity and stability of hiPSC lines is imperative for reliable disease modeling and safe clinical applications of stem cells as a regenerative therapy. Aberrant cytogenetic errors that arise during reprogramming of somatic cells and/or during maintenance, expansion and prolonged culture of hiPSCs will impact the accuracy of in vitro disease modelling or, more critically, the in vivo utility of iPSCs for regenerative medicine. It is important that iPSCs in clinical use are free from cancer-associated genomic aberrations, especially given that several studies have reported chromosomal aneuploidy, translocations, duplications and deletions, and point mutations in iPSCs. The highly aneuploidy human embryonal carcinoma (EC) stem cells, which are the malignant analogues of normal hESCs, typically contain amplified regions of the short arm of chromosome 12 and gains of chromosomes 1, 17 and X.

Increased sub-chromosomal copy number variations (CNVs) with differences in early, intermediate or late passage numbers, deletions associated with tumor-suppressor genes, and duplications of oncogenes have all been reported in iPSCs In most of these studies, the genomic abnormalities in the iPSC lines have been generated from integrating reprogramming methods. To date, however, no systematic and well-controlled (similar reprogramming and stem cell culture methods) reports of recurrent sub-chromosomal abnormalities specific to large numbers of fibroblast- or blood-derived hiPSC lines have been described. The Inventors have developed an iPSC core facility with extensive experience producing, characterizing and differentiating human iPSC lines. This bio-repository currently has over 160 well-characterized individual donor human iPSC lines with multiple clones (2-6) per cell line. The iPSC Core has systematically monitored the genomic stability of hiPSCs derived in the Core from 450 independent iPSC cultures over multiple passages, which have been derived from fibroblast, peripheral blood mononuclear cells, immortalized lymphoblastoid cell lines and primary epithelial cells.

Blood appears to an advantageous alternative for iPSC derivation as widely used in clinical diagnostics, involving less invasive methods of collection that is standardized and less traumatic than skin biopsy. The major components of peripheral blood (PB) are red blood cells and platelets. White blood cells are the nucleated cells in PB at concentrations of 3.6-11×10$^6$/ml. Mature T cells and primary progenitor cells in PB can be readily expanded using established methods and are among the most successfully-used sources for reprogramming. T cells are the most abundant cells after granulocytes in PB (20-30%) and T cells can be readily expanded with IL-2 and anti-CD3/CD28 microbeads. Reprogramming of T cells into pluripotency has been reported by many labs using different approaches for the sake of developing replacements to aged T cells for immunotherapy. However, mature T cells harbor a single T cell receptor (TCR) after somatic recombination and have lost the ability to regenerate the T cell repertoire with unlimited possibilities.

Here the Inventors have developed a reliable protocol to efficiently reprogram blood cells (BCs) including peripheral mononuclear blood cells (PBMCs) into iPSCs (BC-iPSCs) and show that these iPSC lines are superior in terms of cytogenetic stability in comparison to their fibroblast-derived iPSC (Fib-iPSCs) lines obtained from public repositories or local clinics. The Inventors describe methods and cytogenetic stability for derivation of BC-iPSCs from both a lymphoid T cell and a myeloid non-T cell population. The Inventors discovered that hiPSC lines generated from PBMCs using non-integrating methods have greatly lower incidences of genomic aberrations than those generated by integrating methods. Both fib-iPSCs and BC-iPSCs derived from the same somatic cells contained comparable numbers of de novo CNVs. Our results show that freshly isolated human PBMCs can be faithfully reprogrammed to pluripotency with greater cytogenetic stability using episomal plasmids. As such, PBMCs should be a preferred somatic cell source for iPSC reprogramming to minimize any effects of acquired genomic aberrations and, further, should be considered as an ideal cell source for regenerative medicine.

In contrast to mature T or B cells, the alternative source of blood progenitors contain an intact genome. In addition, they can be expanded in culture conditions that favor the proliferation of myeloid cells or erythroid cells. Blood stem/progenitor cells express surface marker CD34 and reside in the stem cell niche. However, only about 1% stem/progenitor cells enter circulation each day and as a result, only 0.01-0.1% cells in PB are CD34+ cells. This population can be enriched by magnetic-activated cell sorting (MACS) or culture of MNCs for several days can be relied upon to expand CD34+ cells to a 5-20% purity, which can be used for reprogramming without further purification.

Other nucleated peripheral blood cells include granulocytes (mostly neutrophils), monocytes, T lymphocytes, B lymphocytes and a few progenitor cells. Focusing on these constitutes of blood can be achieved by depleting red blood cells and platelet using lysis buffer followed by multiple centrifugations. Ficoll gradient centrifugation can also be utilized to deplete both red blood cells and granulocytes, leading to the enrichment of mononuclear cells (MNCs). Against this backdrop, reprogramming with exogenously expressed factors is notoriously inefficient and requires multiple cell cycles to achieve pluripotency. As such, primary granulocytes, monocytes and B lymphocytes are among the most difficult cells to be reprogrammed due to the lack of reliable protocols to expand these cells. Primary success in this area includes Epstein-Barr virus immortalized lymphoblastoid B cells can be readily expanded in ex vivo culture and thus be reprogrammed to pluripotency.

In view of the above, of great interest is reprogramming of the non-T cell component of blood. Existing techniques are largely unable to reprogram this population from isolated peripheral blood mononuclear cells (PBMCs). More specifically, PBMCs are any peripheral blood cell having a round nucleus. This includes lymphocytes (T cells, B cells, NK cells), monocytes, dendritic cells. Lymphocytes are Small (5-10 µm) and Medium (10-18 µm) and constitute 70-90% of PBMCs. Of these cells, 70-85% CD3+ T cells (40-70% of PBMCs), CD4 Helper T cells (25-60% of PBMCs), typically with CD4 to CD8 ratio of 2:1, CD8 "Cytotoxic" compartment T cells (5-30% of PBMCs). The remaining compartment includes 5-20% B Cells (up to 15% of PBMCs) and 5-20% NK Cells (up to 15% of PBMCs). Monocytes are 16-25 µm and 10-30% of PBMCs (macrophages). Dendritic cells: 1-2% of PBMCs These described approaches allow for use of peripheral blood as a readily accessible resource for cellular reprogramming with superior properties in genomic and karyotype stability avoiding environmental insults for which mutations or other forms of structural alteration would otherwise be therapeutic materials derived therein.

As described, the Inventors have established improved techniques for highly efficient, reproducible reprogramming using non-integrating episomal plasmid vectors, including generation of iPSCs from blood cells, including whole blood and peripheral blood, the resulting reprogrammed pluripotent cells described herein as "BC-iPSCs".

Generally, different approaches for non-integrative reprogramming span at least categories: 1) integration-defective viral delivery, 2) episomal delivery, 3) direct RNA delivery, 4) direct protein delivery and 5) chemical induction. As described further herein, the adoption of episomal vectors allows for generation of iPSCs substantially free of the vectors used in their production, as episomal or similar vectors do not encode sufficient viral genome sufficient to give rise to infection or a replication-competent virus. At the same time, these vectors do possess a limited degree of self-replication capacity in the beginning somatic host cells. This self-replication capacity provides a degree of persistent expression understood to be beneficial in allowing the dedifferentiation process to initiate take hold in a target host cell.

One example of a plasmid vector satisfying these criteria includes the Epstein Barr oriP/Nuclear Antigen-1 ("EBNA1") combination, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs.

More specifically, persistent expression of reprogramming factor encoded in an oriP/EBNA1 vector occurs across multiple cell divisional cycles. Sufficiently high levels of reprogramming factors across several cell divisions allows for successful reprogramming even after only one infection. While sustained expression of reprogramming factors is understood to be beneficial during initial programming stages, otherwise unlimited constitutive expression would hamper subsequent stages of the reprogramming process. For example, unabated expression of reprogramming factors would interfere with subsequent growth, development, and fate specification of the host cells.

At the same time, a further benefit is the eventual removal of the reprogramming factor transgenes, as a small portion of episomes is lost per cell cycle. This is due to the asymmetric replication capacity of the host cell genome and episomal self-replication and it is estimated that approximately 0.5% of vector is lost per generation. Gradual depletion of plasmids during each cell division is inevitable following propagation leading to a population of integration-free iPSCs. The persistent, yet eventual abrogation of reprogramming factor expression on oriP/EBNA1 is highly coincident with the needs for different stages of the reprogramming process and eliminates the need for further manipulation steps for excision of the reprogramming factors, as has been attempted through use of transposons and excisable polycistronic lentiviral vector elements. Although oriP/EBNA1 has been applied by others in reprogramming studies, the reported efficiencies are extremely low (as few as 3 to 6 colonies per million cells nucleofected), which may be due, in-part, to reliance on large plasmids encoding multiple reprogramming factors (e.g., more than 12 kb), negatively impacting transfection efficiency.

In addition to these choices in vector designs, the specific combinations of reprogramming factors implemented in the literature have varied. As mentioned, reprogramming factors that have been used include pluripotency-related genes Oct-4, Sox-2, Lin-28, Nanog, Sal14, Fbx-15 and Utf-1. These factors, traditionally are understood be normally expressed early during development and are involved in the maintenance of the pluripotent potential of a subset of cells that will constituting the inner cell mass of the pre-implantation embryo and post-implantation embryo proper. Their ectopic expression of is believed to allow the establishment of an embryonic-like transcriptional cascade that initiates and propagates an otherwise dormant endogenous core pluripotency program within a host cell. Certain other reprogramming determinants, such as Tert, Klf-4, c-Myc, SV40 Large T Antigen ("SV40LT") and short hairpin RNAs targeting p53 ("shRNA-p53") have been applied. There determinants may not be potency-determining factors in and of themselves, but have been reported to provide advantages in reprogramming. For example, TERT and SV40LT are understood to enhance cell proliferation to promote survival during reprogramming, while others such as short hairpin targeting of p53 inhibit or eliminate reprogramming barriers, such as senescence and apoptosis mechanisms. In each case, an increase in both the speed and efficiency of reprogramming is observed. In addition, microRNAs ("miRNAs") are also known to influence pluripotency and reprogramming, and some miRNAs from the miR-290 cluster have been applied in reprogramming studies. For example, the introduction of miR-291-3p, miR-294 or miR-295 into fibroblasts, along with pluripotency-related genes, has also been reported to increase reprogramming efficiency.

While various vectors and reprogramming factors in the art appear to present multiple ingredients capable of establishing reprogramming in cells, a high degree of complexity occurs when taking into account the stoichiometric expression levels necessary for successful reprogramming to take hold. For example, somatic cell reprogramming efficiency is reportedly fourfold higher when Oct-4 and Sox2 are encoded in a single transcript on a single vector in a 1:1 ratio, in contrast to delivering the two factors on separate vectors. The latter case results in a less controlled uptake ratio of the two factors, providing a negative impact on reprogramming efficiency. One approach towards addressing these obstacles is the use of polycistronic vectors, such as inclusion of an internal ribosome entry site ("IRES"), provided upstream of transgene(s) that is distal from the transcriptional promoter. This organization allows one or more transgenes to be provided in a single reprogramming vector, and various inducible or constitutive promoters can be combined together as an expression cassette to impart a more granular level of transcriptional control for the plurality of transgenes. These more specific levels of control can benefit the reprogramming process considerably, and separate expression cassettes on a vector can be designed accordingly as under the control of separate promoters.

Although there are advantages to providing such factors via a single, or small number of vectors, upper size limitations on eventual vector size do exist, which can stymie attempts to promote their delivery in a host target cell. For example, early reports on the use of polycistronic vectors were notable for extremely poor efficiency of reprogramming, sometimes occurring in less than 1% of cells, more typically less than 0.1%. These obstacles are due, in-part, to certain target host cells possessing poor tolerance for large constructs (e.g., fibroblasts), or inefficient processing of IRES sites by the host cells. Moreover, positioning of a factor in a vector expression cassette affects both its stoichiometric and temporal expression, providing an additional variable impacting reprogramming efficiency. Thus, some improved techniques can rely on multiple vectors each encoding one or more reprogramming factors in various expression cassettes. Under these designs, alteration of the amount of a particular vector for delivery provides a coarse, but relatively straightforward route for adjusting expression levels in a target cell.

A further advantage of the techniques described herein is the use of defined media conditions for the reprogramming process, including the use of ESC media and/or E7 media. While certain additives may be present to spur the reprogramming process (e.g., L-Ascorbic Acid, Transferrin, Sodium Bicarbonate, Insulin, Sodium Selenite and/or bFGF), no serum or animal components are used. In some instances, there may be further benefits in altering the chemical and/or atmospheric conditions under which reprogramming will take place. For example, as the pre-implantation embryo is not vascularized and hypoxic (similar to bone marrow stem-cell niches) reprogramming under hypoxic conditions of 5% $O_2$, instead of the atmospheric 21% $O_2$, may further provide an opportunity to increase the reprogramming efficiency. Similarly, chemical induction techniques have been used in combination with reprogramming, particularly histone deacetylase (HDAC) inhibitor molecule, valproic acid (VPA), which has been found wide use in different reprogramming studies. At the same time, other small molecules such as MAPK kinase (MEK)-ERK ("MEK") inhibitor PD0325901, transforming growth factor beta ("TGF-β") type I receptor ALK4, ALK5 and ALK7 inhibitor SB431542 and the glycogen synthase kinase-3 ("GSK3") inhibitor CHIR99021 have been applied for activation of differentiation-inducing pathways (e.g. BMP signaling), coupled with the modulation of other pathways (e.g. inhibition of the MAPK kinase (MEK)-ERK pathway) in order to sustain self-renewal. Other small molecules, such as Rho-associated coiled-coil-containing protein kinase ("ROCK") inhibitors, such as Y-27632 and thiazovivin ("Tzv") have been applied in order to promote survival and reduce vulnerability of pSCs to cell death, particularly upon single-cell dissociation.

In addition to the choice of delivery vectors, reprogramming factor combinations, and conditions for reprogramming, further variations must consider the nature of the host target cell for reprogramming. To date, a wide variety of cells have served as sources for reprogramming including fibroblasts, stomach and liver cell cultures, human keratinocytes, adipose cells, and frozen human monocyte. Clearly, there is a wide and robust potential for dedifferentiation across many tissues sources. Nevertheless, it is widely understood that depending on the donor cell type, reprogramming is achieved with different efficiencies and kinetics. For example, although fibroblasts remain the most popular donor cell type for reprogramming studies, other types of cells such as human primary keratinocytes transduced with Oct-4, Sox-2, Klf-4 and c-Myc have been reported to reprogram 100 times more efficiently and twofold faster. Additionally, some other cell types, such as cord blood cells, may only require a subset of reprogramming factors, such as Oct-4 and Sox-2 for dedifferentiation to take hold, while neural progenitor cells may only require Oct-4. Without being bound to any particular theory, it is believed that differences in reprogramming efficiency and/or reprogramming factor requirements of specific host cells result from high endogenous levels of certain reprogramming factors and/or intrinsic epigenetic states that are more amenable to reprogramming.

Although these many other sources have been used across studies for the generation of iPSCs, mononuclear cells (MNCs) from peripheral blood (PB) are a highly attractive host cell candidate due to convenience and features as an almost unlimited resource for cell reprogramming. PB cells in particular are relatively easy to isolate (e.g., blood draw) compared to isolation from other sources such as fibroblasts (e.g., skin biopsy). These cells do not require laborious culturing and propagation prior to reprogramming, thereby reducing the overall time from which reprogramming iPSCs can be obtained.

Following successful reprogramming, clonal selection allows for generation of pluripotent stem cell lines. Ideally, such cells possess requisite morphology (i.e., compact colony, high nucleus to cytoplasm ratio and prominent nucleolus), self-renewal capacity for unlimited propagation in culture (i.e., immortal), and with the capability to differentiate into all three germ layers (e.g., endoderm, mesoderm and ectoderm). Further techniques to characterize the pluripotency of a given population of cells include injection into an immunocompromised animal, such as a severe combined immunodeficient ("SCID") mouse, for formation of teratomas containing cells or tissues characteristic of all three germ layers.

Described herein is a composition of blood cell derived induced pluripotent stem cells ("BC-iPSCs"). In certain embodiments, the composition of blood cell derived induced pluripotent stem cells includes cells generated by providing a quantity of blood cells, delivering a quantity of reprogramming factors into the blood cells, culturing the blood cells in a reprogramming media for at least 4 days, wherein delivering the reprogramming factors, and culturing generates the blood cells derived induced pluripotent stem cells. In certain embodiments, the blood cells are T-cells. In other embodiments, the blood cells are non-T-cells. In other embodiments, the blood cells are mononuclear cells (MNCs), including for example peripheral blood mononuclear cells (PBMCs). In other embodiments, the cells are primary granulocytes, monocytes and B lymphocytes.

In certain embodiments, the reprogramming factors are Oct-4, Sox-2, Klf-4, c-Myc, Lin-28, SV40 Large T Antigen ("SV40LT"), and short hairpin RNAs targeting p53 ("shRNA-p53"). In other embodiments, these reprogramming factors are encoded in a combination of vectors including pEP4 E02S ET2K, pCXLE-hOCT3/4-shp53-F, pCXLE-hSK, pCXLE-hUL and pCXWB-EBNA1. This includes, for example, using about 0.5-1.0 ug pCXLE-hOCT3/4-shp53, 0.5-1.0 ug pCXLE-hSK, 0.5-1.0 ug pCXLE-UL, about 0.25-0.75 ug pCXWB-EBNA1 and 0.5-1.0 ug pEP4 E02S ET2K. This includes, for example, using 0.83 ug pCXLE-hOCT3/4-shp53, 0.83 ug pCXLE-hSK, 0.83 ug pCXLE-UL, 0.5 ug pCXWB-EBNA1 and 0.83 ug pEP4 E02S ET2K, wherein the stoichiometric ratio of SV40LT (encoded in pEP4 E02S ET2K) and EBNA-1 (encoded in pCXWB-EBNA1) supports the reprogramming of non-T cell component of blood, including peripheral blood mononuclear cells. In certain other embodiments, the reprogramming media includes PD0325901, CHIR99021, HA-100, and A-83-01. In other embodiments, the culturing the blood cells in a reprogramming media is for 4-30 days. In various embodiments, the blood cells are plated on a treated cell culture surface after delivering a quantity of reprogramming factors. In various embodiments, treatment includes plating of feeder cells, such as mouse embryonic fibroblasts. In other embodiments, treatment includes coating with extracellular matrix proteins. In various embodiment, extracellular matrix proteins include laminin.

In various embodiments, the BC-iPSCs are capable of serial passaging as a cell line. In various embodiments, the BC-iPSCs possess genomic stability. Genomic stability can be ascertained by various techniques known in the art. For example, G-band karyotyping can identify abnormal cells lacking genomic stability, wherein abnormal cells possess about 10% or more mosaicism, or one or more balanced translocations of greater than about 5, 6, 7, 8, 9, 10 or more Mb. Alternatively, genomic stability can be measured using comparative genomic hybridization (aCGH) microarray, comparing for example, BC-iPSCs against iPSCs from a non-blood cell source such as fibroblasts. Genomic stability can include copy number variants (CNVs), duplications/deletions, and unbalanced translocations. In various embodiments, BC-iPSCs exhibit no more than about 3, 4, 5, 6, 7, 8, 9, 10, 11, 12, 13, 15, 16, 17, 18, 19, or 20 Mb average size of amplification and deletion. In various embodiments, BC-iPSCs exhibit no more than about 20-30 Mb average size of amplification and deletion. In various embodiments, BC-iPSCs exhibit no more than about 30-40 Mb average size of amplification and deletion. In various embodiments, BC-iPSCs exhibit no more than about 40-50 Mb average size of amplification and deletion. In various embodiments, the average number of acquired de novo amplification and deletions in BC-iPSCs is less than about 5, 4, 3, 2, or 1. For example, de novo amplification and deletions in fib-iPSCs are at least two-fold greater than in PBMC-iPSCs.

In different embodiments, reprogramming factors can also include one or more of following: Oct-4, Sox-2, Klf-4, c-Myc, Lin-28, SV40LT, shRNA-p53, nanog, Sal14, Fbx-15, Utf-1, Tert, or a Mir-290 cluster microRNA such as miR-291-3p, miR-294 or miR-295. In different embodiments, the reprogramming factors are encoded by a vector. In different embodiments, the vector can be, for example, a non-integrating episomal vector, minicircle vector, plasmid, retrovirus (integrating and non-integrating) and/or other genetic elements known to one of ordinary skill. In different embodiments, the reprogramming factors are encoded by one or more oriP/EBNA1 derived vectors. In different embodiments, the vector encodes one or more reprogramming factors, and combinations of vectors can be used together to deliver one or more of Oct-4, Sox-2, Klf-4, c-Myc, Lin-28, SV40LT, shRNA-p53, nanog, Sal14, Fbx-15, Utf-1, Tert, or a Mir-290 cluster microRNA such as miR-291-3p, miR-294 or miR-295. For example, oriP/EBNA1 is an episomal vector that can encode a vector combination of multiple reprogramming factors, such as pCXLE-hUL, pCXLE-hSK, pCXLE-hOCT3/4-shp53-F, pEP4 EO2S T2K and pCXWB-EBNA1.

In other embodiments, the reprogramming factors are delivered by techniques known in the art, such as nuclefection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell.

In various embodiments, the reprogramming media is embryonic stem cell (ESC) media. In various embodiments, the reprogramming media includes bFGF. In various embodiments, the reprogramming media is E7 media. In various embodiments, the reprogramming E7 media includes L-Ascorbic Acid, Transferrin, Sodium Bicarbonate, Insulin, Sodium Selenite and/or bFGF In different embodiments, the reprogramming media comprises at least one small chemical induction molecule. In different embodiments, the at least one small chemical induction molecule comprises PD0325901, CHIR99021, HA-100, A-83-01, valproic acid (VPA), SB431542, Y-27632 or thiazovivin ("Tzv"). In different embodiments, culturing the BCs in a reprogramming media is for at least 4, 5, 6, 7, 8, 9, 10, 11, 12, 13, 14, 15, 16, 17, 18, 19, 20, 21, 22, 23, 24, 25, 26, 27, 28, 29, or 30 days.

In certain embodiments, the BC-iPSCs are derived from blood cells previously isolated from a subject, by for, example, drawing a blood sample from the subject. In other embodiments, the blood cells are isolated from a subject possessing a disease mutation. For example, subjects possessing any number of mutations, such as autosomal dominant, recessive, sex-linked, can serve as a source of blood cells to generate BC-iPSCs possessing said mutation. In other embodiments, the disease mutation is associated with a neurodegenerative disease, disorder and/or condition. In other embodiments, the disease mutation is associated with an inflammatory bowel disease, disorder, and/or condition. In various embodiments, the BC-iPSCs possess features of pluripotent stem cells. Some exemplary features of pluripotent stem cells including differentiation into cells of all three germ layers (ectoderm, endoderm, mesoderm), either in vitro or in vivo when injected into an immunodeficient animal, expression of pluripotency markers such as Oct-4, Sox-2, nanog, TRA-1-60, TRA-1-81, SSEA4, high levels of alkaline phosphatase ("AP") expression, indefinite propagation in culture, among other features recognized and appreciated by one of ordinary skill.

Other embodiments include a pharmaceutical composition including a quantity of blood cells derived induced pluripotent stem cells generated by the above described methods, and a pharmaceutically acceptable carrier.

Also described herein is an efficient method for generating induced pluripotent stem cells, including providing a quantity of cells, delivering a quantity of reprogramming factors into the cells, culturing the cells in a reprogramming media for at least 4 days, wherein delivering the reprogramming factors, and culturing generates induced pluripotent stem cells. In certain embodiments, the cells are primary culture cells. In other embodiments, the cells are blood cells (BCs). In certain embodiments, the blood cells are T-cells. In other embodiments, the blood cells are non-T-cells. In other embodiments, the cells are mononuclear cells (MNCs), including for example peripheral blood mononuclear cells (PBMCs). In other embodiments, the cells are primary granulocytes, monocytes and B lymphocytes.

In certain embodiments, the reprogramming factors are Oct-4, Sox-2, Klf-4, c-Myc, Lin-28, SV40 Large T Antigen ("SV40LT"), and short hairpin RNAs targeting p53 ("shRNA-p53"). In other embodiments, these reprogramming factors are encoded in a combination of vectors including pEP4 E02S ET2K, pCXLE-hOCT3/4-shp53-F, pCXLE-hSK, pCXLE-hUL and pCXWB-EBNA1. This includes, for example, using about 0.5-1.0 ug pCXLE-hOCT3/4-shp53, 0.5-1.0 ug pCXLE-hSK, 0.5-1.0 ug pCXLE-UL, about 0.25-0.75 ug pCXWB-EBNA1 and 0.5-1.0 ug pEP4 E02S ET2K. This includes, for example, using 0.83 ug pCXLE-hOCT3/4-shp53, 0.83 ug pCXLE-hSK, 0.83 ug pCXLE-UL, 0.5 ug pCXWB-EBNA1 and 0.83 ug pEP4 E02S ET2K, wherein the stoichiometric ratio of SV40LT (encoded in pEP4 E02S ET2K) and EBNA-1 (encoded in pCXWB-EBNA1) supports the reprogramming of non-T cell component of blood, including peripheral blood mononuclear cells. In various embodiments, the reprogramming media is embryonic stem cell (ESC) media. In various embodiments, the reprogramming media includes bFGF. In various embodiments, the reprogramming media is E7 media. In various embodiments, the reprogramming E7 media includes L-Ascorbic Acid, Transferrin, Sodium Bicarbonate, Insulin, Sodium Selenite and/or bFGF. In different embodiments, the reprogramming media comprises at least one small chemical induction molecule. In certain other embodiments, the reprogramming media includes PD0325901, CHIR99021, HA-100, and A-83-01. In other embodiments, the culturing the blood cells in a reprogramming media is for 4-30 days.

In various embodiments, the BC-iPSCs are capable of serial passaging as a cell line. In various embodiments, the BC-iPSCs possess genomic stability. Genomic stability can be ascertained by various techniques known in the art. For example, G-band karyotyping can identify abnormal cells lacking genomic stability, wherein abnormal cells possess about 10% or more mosaicism, or one or more balanced translocations of greater than about 5, 6, 7, 8, 9, 10 or more Mb. Alternatively, genomic stability can be measured using comparative genomic hybridization (aCGH) microarray, comparing for example, BC-iPSCs against iPSCs from a non-blood cell source such as fibroblasts. Genomic stability can include copy number variants (CNVs), duplications/deletions, and unbalanced translocations. In various embodiments, BC-iPSCs exhibit no more than about 3, 4, 5, 6, 7, 8, 9, 10, 11, 12, 13, 15, 16, 17, 18, 19, or 20 Mb average size of amplification and deletion. In various embodiments, BC-iPSCs exhibit no more than about 20-30 Mb average size of amplification and deletion. In various embodiments, BC-iPSCs exhibit no more than about 30-40 Mb average size of amplification and deletion. In various embodiments, BC-iPSCs exhibit no more than about 40-50 Mb average size of amplification and deletion. In various embodiments, the average number of acquired de novo amplification and deletions in BC-iPSCs is less than about 5, 4, 3, 2, or 1. For example, de novo amplification and deletions in fib-iPSCs are at least two-fold greater than in PBMC-iPSCs. In various embodiments, the methods produces iPSC cell lines collectively exhibiting about 20%, 15%, 10%, 5% or less abnormal karyotypes over 4-8, 9-13, 13-17, 17-21, 21-25, or 29 or more passages when serially passaged as a cell line.

In different embodiments, reprogramming factors can also include one or more of following: Oct-4, Sox-2, Klf-4, c-Myc, Lin-28, SV40LT, shRNA-p53, nanog, Sa114, Fbx-15, Utf-1, Tert, or a Mir-290 cluster microRNA such as miR-291-3p, miR-294 or miR-295. In different embodiments, the reprogramming factors are encoded by a vector. In different embodiments, the vector can be, for example, a non-integrating episomal vector, minicircle vector, plasmid, retrovirus (integrating and non-integrating) and/or other genetic elements known to one of ordinary skill. In different embodiments, the reprogramming factors are encoded by one or more oriP/EBNA1 derived vectors. In different embodiments, the vector encodes one or more reprogramming factors, and combinations of vectors can be used together to deliver one or more of Oct-4, Sox-2, Klf-4, c-Myc, Lin-28, SV40LT, shRNA-p53, nanog, Sa114, Fbx-15, Utf-1, Tert, or a Mir-290 cluster microRNA such as miR-291-3p, miR-294 or miR-295. For example, oriP/ EBNA1 is an episomal vector that can encode a vector combination of multiple reprogramming factors, such as pCXLE-hUL, pCXLE-hSK, pCXLE-hOCT3/4-shp53-F, pEP4 EO2S T2K and pCXWB-EBNA1.

In other embodiments, the reprogramming factors are delivered by techniques known in the art, such as nuclefection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell. In certain embodiments, the cells are treated with sodium butyrate prior to delivery of the reprogramming factors. In other embodiments, the cells are incubated or 1, 2, 3, 4, or more days on a tissue culture surface before further culturing. This can include, for example, incubation on a Matrigel coated tissue culture surface. In other embodiments, the reprogramming conditions include application of norm-oxygen conditions, such as 5% $O_2$, which is less than atmospheric 21% $O_2$.

In various embodiments, the reprogramming media is embryonic stem cell (ESC) media. In various embodiments, the reprogramming media includes bFGF. In various embodiments, the reprogramming media is E7 media. In various embodiments, the reprogramming E7 media includes L-Ascorbic Acid, Transferrin, Sodium Bicarbonate, Insulin, Sodium Selenite and/or bFGF. In different embodiments, the reprogramming media comprises at least one small chemical induction molecule. In different embodiments, the at least one small chemical induction molecule comprises PD0325901, CHIR99021, HA-100, A-83-01, valproic acid (VPA), SB431542, Y-27632 or thiazovivin ("Tzv"). In different embodiments, culturing the BCs in a reprogramming media is for at least 4, 5, 6, 7, 8, 9, 10, 11, 12, 13, 14, 15, 16, 17, 18, 19, 20, 21, 22, 23, 24, 25, 26, 27, 28, 29, or 30 days.

Efficiency of reprogramming is readily ascertained by one of many techniques readily understood by one of ordinary skill. For example, efficiency can be described by the ratio between the number of donor cells receiving the full set of reprogramming factors and the number of reprogrammed colonies generated. Measuring the number donor cells receiving reprogramming factors can be measured directly, when a reporter gene such as GFP is included in a vector encoding a reprogramming factor. Alternatively, indirect measurement of delivery efficiency can be provided by transfecting a vector encoding a reporter gene as a proxy to gauge delivery efficiency in paired samples delivering reprogramming factor vectors. Further, the number of reprogrammed colonies generated can be measured by, for example, observing the appearance of one or more embryonic stem cell-like pluripotency characteristics such as alkaline phosphatase (AP)-positive clones, colonies with endogenous expression of transcription factors Oct or Nanog, or antibody staining of surface markers such as Tra-1-60. In another example, efficiency can be described by the kinetics of induced pluripotent stem cell generation. For example, efficiency can include producing cell lines of normal karyotype, including the method producing iPSC cell lines collectively exhibiting about 20%, 15%, 10%, 5% or less abnormal karyotypes over 4-8, 9-13, 13-17, 17-21, 21-25, or 29 or more passages when serially passaged as a cell line.

EXAMPLE 1

General iPSC Reprogramming Protocol for Blood

Generally, the reprogramming method involves the following steps. Frozen peripheral blood mononuclear cells (PBMCs), or freshly isolated PBMCs can be used. Treated cell culture surfaces can be used for plating thawed or freshly isolated PBMS. This includes, for example, cell culture surfaces treated with mouse embryonic feeders (MEF) or extracellular matrix laminin L-521A. An expression plasmid mixture is provided, with the plasmid mixture encoding a combination of pluripotency factors. Plasmids are introduced to PBMCs, by using for example, nucleofection, and thereafter placed on the treated cell culture surface. After 2 days of culturing, reprogramming media is introduced, and replenished until colonies are formed.

EXAMPLE 2

Peripheral Blood Collection and Minimal Processing for Reprogramming

The Inventors have established processes to isolate lymphocytes from freshly collected or commercial sources of human or mammalian peripheral blood (PB). The preferred format for the collection and shipment of such samples is the CPT tubes. This format allows the supplier to centrifuge the vacutainer(s) and separate the red blood cells from the plasma components prior to shipping. The protocol provides for the isolation of PBMCs from the plasma layer of the CPT tubes.

Optional tests: Prior to opening the Vacutainer, several disease state tests can be performed, including testing for HIV, Hepatitis B and C, and syphilis. The latter test results should be made available within 1-3 working days from the collection date. If there is a positive result, the sample(s) will be properly discarded, and all laboratory equipment that was used to process the samples will be decontaminated.

EXAMPLE 3

Collection Procedure (1) Red blood cells and platelets are depleted using containers. BD Vacutainer® CPT™ Tube with Sodium Citrate should be at room temperature (18-25° C.) and properly labeled for patient identification. Spray the CPT Vacutainer lightly with 70% isopropanol/ethanol, wipe the alcohol off.

(2) Blood collection is into three (3) 8 ml CPT tubes per sample using the standard technique for BD Vacutainer® Evacuated Blood Collection Tubes. After collection, tube is stored upright at room temperature until centrifugation. Blood samples should be centrifuged within two hours of blood collection for best results.

(3) Tube/blood sample is centrifuged at room temperature (18-25° C.) in a horizontal rotor (swing-out head) for a minimum of 20 minutes (up to 30 minutes) at 1500 to 1800 RCF (Relative Centrifugal Force).

(4) For blood shipped in CPT tubes and reprogramming is performed within 24 hours: After centrifugation, mononuclear cells and platelets will be in a whitish layer just under the plasma layer (see FIG. 1). An alternative procedure for recovering the separated mononuclear cells is to resuspend the cells into the plasma by inverting the unopened BD Vacutainer® CPT™ Tube gently 5 to 10 times. This is the preferred method for storing or transporting the separated sample for up to 24 hours after centrifugation.

EXAMPLE 4

Important Parameters

Temperature: Since the principle of separation depends on a density gradient, and the density of the components varies with temperature, the temperature of the system should be controlled between 18-25° C. during separation.

Centrifugation: Since the principle of separation depends on the movement of formed elements in the blood through the separation media, the "RCF" should be controlled at 1500 RCF to 1800 RCF. The time of centrifugation should be a minimum of 20 minutes. (As noted in the trouble shooting section, some specimens may require up to 30 minutes for optimal separation.) Centrifugation of the BD Vacutainer® CPT™ Tube up to 30 minutes has the effect of reducing red blood cell contamination of the mononuclear cell fraction. Centrifugation beyond 30 minutes has little additional effect. The BD Vacutainer® CPT™ Tube may be re-centrifuged if the mononuclear "band" or layer is not disturbed.

Time: Blood samples should be centrifuged or separated within two hours of blood drawing. Red blood cell contamination in the separated mononuclear cell fraction increases with longer delays in sample separation. Mononuclear cell recovery decreases with increased time delay before centrifugation, falling to approximately 40% mononuclear cell recovery at 24 hours. Pour the contents (the plasma layer) off into an appropriately labeled 50 mL tube.

EXAMPLE 5

Reprogramming Procedure Materials and Supplies

Described herein is the procedure for reprogramming separated whole blood samples (peripheral blood mononuclear cells—PBMCs) for iPSC generation. Materials for use include: Sterile 1.5 ml Eppendorf tubes; Sterile pipette tips (1000 ul, 200 ul, 10 ul); Amaxa Nucleofector™ 2b Device (Lonza); Human T-Cell Nucleofector Kit (Lonza, Cat #VPA-1002); Prepared MEF 6-well TC Plates or L-521 Coated Plates; 0.22 um SteriFlip (optional); Primate ESC Medium or E7 Medium, described below in Tables 1-4.

Reprogramming Plasmids used include (1) pCXLE-hOCT3/4-shp53; (2) pCXLE-hSK; (3) pCXLE-UL; (4) pCXWB-EBNA1; (5) pEP4 E02S ET2K.

TABLE 1

αβ T-Cell Media

| ITEM | CONCENTRATION |
|---|---|
| | X-vivo10 |
| IL-2 | 30 U/ml |
| Dynabeads Human T-activator CD3/CD28 (to be added after Nucleofection) | 5 ul/well |

TABLE 2

Non-T Cell Media

| ITEM | CONCENTRATION |
|---|---|
| | αMEM |
| FBS | 10% |
| IL-3 | 10 ng/ml |
| IL-6 | 10 ng/ml |
| G-CSF | 10 ng/ml |
| GM-CSF | 10 ng/ml |

TABLE 3

MEF Media (optional)

| ITEM | CONCENTRATION |
|---|---|
| | DMEM |
| FBS | 10% |
| NEAA | 1% |
| GlutaMax | 1% |

TABLE 4

Prepared Primate ESC Medium (Optional)

| ITEM | CONCENTRATION |
|---|---|
| | Primate ESC Medium |
| bFGF | 5 ng/ml |

TABLE 5

Prepared E7 Medium (Optional)

| ITEM | CONCENTRATION |
|---|---|
| | DMEM/F12 |
| L-Ascorbic Acid | 64 ug/ml |
| Transferrin | 10.7 ug/ml |
| Sodium Bicarbonate | 543 ug/ml |
| Insulin | 19.4 ug/ml |
| Sodium Selenite | 14 ng/ml |
| bFGF | 100 ng/ml |

EXAMPLE 6

Reprogramming Procedure

Day −1—Preparation of Plates
MEF Plates—
1. Coat each well of 6-well plate with 1 ml of 0.1% Gelatin. 2. Incubate plate at 37° C. for a minimum of 1 hour. 3. Obtain a vial of frozen MEFs from the LN2 tank. 4. Thaw vial in a water bath by gently moving the frozen vial in a FIG. 8 motion in the water. 5. Collect thaw cells into a 15 ml conical. 6. Slowly add MEF media to bring the volume to 10 mls. 7. Centrifuge tube/MEFs at room temperature (18-25° C.) at 1000 to 1200 RPM (Relative Centrifugal Force) for 5 minutes. 8. While the cells are spinning, aspirate the gelatin from the 6-well plate and add 1 ml of MEF media to each well. 9. After the centrifuged has stopped, remove the conical and aspirate the supernatant without disturbing the cell pellet. 10. Resuspend the cell pellet in enough MEF media to achieve approximately 50,000 cells/ml. 11. Add 1 ml of cell/MEF media mixture to each well. 12. Swirl plate to ensure even distribution of MEFs and place in incubator overnight. 13. Prepare 10 ug/ml of L-521 by thawing one 1 ml vial of 100 ug/ml L-521 and adding the contents to 9 mls of sterile PBS. 14. Filter the mixture through a 0.22 um filter or SteriFlip. 15. Add 1 ml of the 10 ug/ml L-521 mixture to each well of a 6-well plate. 16. Wrap the plate with Parafilm and place in the 37° C. incubator for 2 hours. 17. Remove plate from the incubator and place in 4° C. fridge.

Day 0—Cell Preparation of Frozen PBMCs
18. Thaw 2 frozen vials of PBMCs containing 5e6 cells each in the water bath using a "FIG. 8" motion until a small ball of ice remains. 19. Collect the contents of each tube into two separate sterile 15 ml conicals and label the tubes 1 and 2. 20. Add sterile PBS to each tube to bring the volume to 10 mls. Mix cells by inverting tube 5 times. 21. Centrifuge for 15 minutes at 1000 RPM. 22. Proceed to step 25

Cell Preparation of Freshly Isolated PBMCs

23. Place 3e6 freshly isolated PBMCs into 2 sterile 15 ml conicals each. 24. Perform steps 19 to 22.

Reprogramming

If using L-521 coated plates, one allows plates to equilibrate to room-temperature for at least 1 hr. 25. Prepare a 1.5 ml Eppendorf tubes of Lonza Nucleofection solution according to protocol (82 ul of Nucleofection Solution+18 ul of Supplement per reaction). Label the tube NS.

NOTE: One will be performing each reaction twice; once for T-cell conditions and once for non T-cell conditions. It is okay to prepare a master mix of NS for all reactions.

26. In an 1.5 ml Eppendorf tube, prepare 3.82 ug of expression plasmid mixture for each reaction as follows:

i. pCXLE-hOCT3/4-shp53: 0.83 ug
ii. pCXLE-hSK: 0.83 ug
iii. pCXLE-UL: 0.83 ug
iv. pCXWB-EBNA1: 0.5 ug
v. pEP4 E02S ET2K: 0.83 ug 27. Prepare a 15 ml conical with 6 mls T-cell media. 28. Prepare a 15 ml conical with 6 mls non T-cell media. 29. Aspirate the supernatant from one of the 15 ml conicals containing your cells. 30. Gently flick the tube to loosen up the cell pellet. 31. Add 100 ul of NS mixture to your cell pellet and gently pipette up and down 3-4 times. 32. Transfer the total volume of NS/cell mixture to a 1.5 ml Eppendorf tube containing your plasmid mixture and mix by gently pipetting up and down 3-4 times. 33. Transfer the total volume of NS/cell/plasmid mixture to a glass cuvette provided with the Lonza T-cell kit. 34. Place the cuvette in the Amaxa nucleofector and run program V-024. 35. Using the plastic pipette tip provided with the Lonza T-cell kit, transfer a small amount of T-cell media to the glass cuvette then transfer the entire contents of the cuvette to the 15 ml conical containing 6 mls of T-cell media. 36 Repeat steps 29-34 for your second 15 ml conical containing cells, proceed to step 37.

37. Using the plastic pipette tip provided with the Lonza T-cell kit, transfer a small amount of non T-cell media to the glass cuvette then transfer the entire contents of the cuvette to the 15 ml conical containing 6 mls of non T-cell media.

Plate Down

MEF/Primate ESC condition

38. Remove the MEF media from each of the wells. 39. Rinse each well with 1 ml of sterile PBS. 40. Transfer the entire contents of the 15 ml conical from step 35 to the top 3 wells by adding 2 mls to each well. 41. Add 5 ul of Dynabeads Human T-activator CD3/CD28 to each well. 42. Transfer the entire contents of the 15 ml conical from step 37 to the bottom 3 wells by adding 2 mls to each well. 43. Place the plate in a 37° C. incubator.

L-521/E7 Condition

44. Aspirate the L-521 from each well. 45. Transfer the entire contents of the 15 ml conical from step 5.35 to the top 3 wells by adding 2 mls to each well. 46. Add 5 ul of Dynabeads Human T-activator CD3/CD28 to each well. 47. Transfer the entire contents of the 15 ml conical from step 37 to the bottom 3 wells by adding 2 mls to each well. 48. Place the plate in a 37° C. incubator.

Day 2

49. On day 2 post nucleofection, add 2 mls of the appropriate reprogramming media (Primate ESC+bFGF or E7) to each well. DO NOT ASPIRATE ANYTHING FROM THE WELLS.

Day 4-25+

50. Beginning on day 4, gently aspirate the media from each well and add 2 mls fresh reprogramming media to each well. This will be done every other day.

Day 25+

51. Using a pulled glass pipette, isolate individual colonies and transfer single colonies into 1 well of 12-well dish containing the appropriate substrate.

EXAMPLE 7

A variety of quality control assays can be performed to confirm proper generation of pluripotent stem cells. Examples of such tests exemplifying desirable characteristics of pSC generation are presented in Table 1.

TABLE 1 iPSC QC Assays

| Test | Assay/Kit | Result |
|---|---|---|
| Mycoplasma Testing | MycoAlert - Lonza | Negative |
| Alkaline Phosphatase (AP) Staining | Alkaline Phosphatase Staining Kit II - Stemgent | Positive |
| Immunocytochemistry (ICC) for Pluripotency Markers - Oct, SSEA4, Nanog, Tra-1-60, Tra-1-81 | ICC Staining | Positive |
| Endogenous pluripotency genes turned on - OCT4, SOX2, LIN28, KLF4, L-myc | qPCR | Positive gene expression |
| Lack of exogenous gene presence | qPCR | Negative gene expression |
| G-Band Karyotype | N/A | Normal Human Karyotype |
| Illumina gene-chip expression and bioinformatics assay | Pluritest | Pluripotency score >20, Novelty score <1.6 |
| EB Formation and Tri-lineage gene expression | TaqMan_hPSC Scorecard - Life Technologies | Positive for Endoderm, Ectoderm and Mesoderm |
| Short tandem repeat (STR) profile and interspecies contamination testing | Cell Check 9 - IDEXX | Genetic profile of the sample matches identically to the parental genetic profile. Samples are confirmed to be of human origin and no mammalian interspecies contamination is detected. |
| T-Cell Clonality Assay (for whole blood derived iPSC lines) | TCRB + TCRG T-Cell Clonality Assay™ Gel Detection - Invivoscribe | Presence (T-cell) of lack of clonal TCR beta gene rearrangements (non T-cell) |

EXAMPLE 8

Alkaline Phosphatase Staining

For characterization of BC-iPSCs, Alkaline Phosphatase staining can be performed using the Alkaline Phosphatase Staining Kit II (Stemgent, Cat no. 00-0055) according to the manufacturer's instructions.

EXAMPLE 9

Immunohisto/Cytochemistry

For further characterization of BC-iPSCs, BC-iPSCs or differentiated cells can be plated on glass coverslips or optical-bottom 96-well plates (Thermo, #165305) and subsequently fixed in 4% paraformaldehyde. Intestinal organoids can be fixed in 4% paraformaldehyde, transferred to 30% sucrose, embedded in HistoPrep (Thermo Fisher Scientific) and cut into 20 μm sections. All cells are blocked in 510% goat or donkey serum with 0.1% Triton X-100 and incubated with primary antibodies either for either 3 hrs at room temperature or overnight at 4° C. Cells are then rinsed and incubated in species-specific AF488 or AF594-conjugated secondary antibodies followed by Hoechst 33258 (0.5 μg/ml; Sigma) to counterstain nuclei.

Antibodies suitable for immunocytochemistry and immunoblotting include: (as listed by antigen, dilution, catalog no., isotype, and manufacturer) SSEA4, 1:250, MAB4304, mIgG3, Millipore; TRA-1-60, 1:250, 09-0010, IgM, Stemgent; TRA-1-81, 1:250, 09-0011, mIgM, Stemgent; OCT4, 1:250, 09-0023, Rabbit IgG, Stemgent; NANOG, 1:250, 09-0020, Rabbit IgG, Stemgent; SOX2, 1:500, AB5603, Rabbit IgG, Millipore; TuJ1 (β3-tubulin), 1:1000, T8535, mIgG2b, Sigma; CDX2, 1:500, NBP1-40553, IgG, Novus; FABP2, 1:500, AF3078, IgG, R & D systems; Collagen Type 1, 1:500, 600-401-103-0.1, Rabbit Rockland; CD73, 1:500, 550257, mIgG1, BD Pharmingen; NKX6.1, 1:100 F55A10, mIgG1, DSHB Iowa; HB9, 1:25, 81.5C10, mIgG1, DSHB Iowa; ISELT1, 1:250, AF1837, Goat IgG, R & D systems; SMI32, 1:1000, SMI-32R, mIgG1, Covance; CHAT, 1:250, AB144P, Goat IgG, Millipore; SMN, 1:250, 610647, mIgG1, BD Biosciences; Cox-IV, 1:1000, 4850s, Rabbit Cell signaling; GAPDH, 1:1000, ab9484, mIgG2b, Abcam.

EXAMPLE 10

Flow Cytometry

Additional characterization of can include flow cytometry. Specifically, BC-iPSCs are dissociated into a single cell suspension using Accutase (Millipore, #SCR005). Surface staining of IPSCs is carried out using SSEA4 (R&D Systems, FAB1435A).

Cells were then fixed, permeabilized and stained intracellularly for Oct3/4 (BD Pharmingen, 560186). Recommended isotypes are used according to the antibodies recommendation (R&D Systems, FABIC007 and BD Pharmingen, 562547). All samples re analyzed using a BD LSRFortessa flow cytometer using BD FACSDiva software. All images are generated using FloJo software.

EXAMPLE 11

Karyotype

Karyotyping can also be performed as follows. Human BC-iPSCs are incubated in Colcemid (100 ng/mL; Life Technologies) for 30 minutes at 37° C. and dissociated using TrypLE for 10 minutes. They can be washed in phosphate buffered saline (PBS) and incubated at 37° C. in 5 mL hypotonic solution (1 g KCl, 1 g Na Citrate in 400 mL water) for 30 minutes. The cells can be centrifuged for 2.5 minutes at 1500 RPM and resuspended in fixative (methanol: acetic acid, 3:1) at room temperature for 5 minutes. This is repeated twice, and finally cells were resuspended in 500 μl of fixative solution and submitted to the Cedars-Sinai Clinical Cytogenetics Core for G-Band karyotyping.

EXAMPLE 12

PluriTest

Pluritest provides a robust measurement of pluripotency. Total RNA can be isolated using the RNeasy Mini Kit (Qiagen) and subsequently run on a Human HT-12 v4 Expression BeadChip Kit (Illumina). The raw data file (idat file) was subsequently uploaded onto the Pluritest widget online (www.pluritest.org).

EXAMPLE 13

Quantitative RT-PCR

Total RNA was isolated using the RNeasy Mini Kit (Qiagen), and 1 ug of RNA was used to make cDNA using the transcription system (Promega). qRT-PCR was performed using specific primer sequences (Table 2) under standard conditions. "CDS" indicates that primers designed for the coding sequence measured expression of the total endogenous gene expression only, whereas "Pla" indicates that primers designed for the plasmid transgene expression only. Data are represented as mean±SEM

TABLE 2 qRT-PCR Primer Sequences

| Gene Name | Forward Primer | Reverse Primer |
|---|---|---|
| OCT3/4 CDS | ccccagggccccattttggtacc (SEQ ID NO: 1) | acctcagtttgaatgcatgggagagc (SEQ ID NO: 2) |
| OCT3/4 Pla | cattcaaactgaggtaaggg (SEQ ID NO: 3) | tagcgtaaaaggagcaacatag (SEQ ID NO: 4) |
| SOX2 CDS | ttcacatgtcccagcactaccaga (SEQ ID NO: 5) | tcacatgtgtgagaggggcagtgtgc (SEQ ID NO: 6) |
| SOX2 Pla | ttcacatgtcccagcactaccaga (SEQ ID NO: 7) | tttgtttgacaggagcgacaat (SEQ ID NO: 8) |
| KLF4 CDS | acccatccttcctgcccgatcaga (SEQ ID NO: 9) | ttggtaatggageggegggacttg (SEQ ID NO: 10) |

TABLE 2-continued qRT-PCR Primer Sequences

| Gene Name | Forward Primer | Reverse Primer |
| --- | --- | --- |
| KLF4 P1a | ccacctcgccttacacatgaaga (SEQ ID NO: 11) | tagcgtaaaaggagcaacatag (SEQ ID NO: 12) |
| LMYC CDS | gcgaacccaagacccaggcctgctcc (SEQ ID NO: 13) | caggggtctgctcgcaccgtgatg (SEQ ID NO: 14) |
| LMYC P1a | ggctgagaagaggatggctac (SEQ ID NO: 15) | tttgtttgacaggagcgacaat (SEQ ID NO: 16) |
| LIN28 CDS | agccatatggtagcctcatgtccgc (SEQ ID NO: 17) | tcaattctgtgcctccgggagcagggtagg (SEQ ID NO: 18) |
| LIN28 P1a | agccatatggtagcctcatgtccgc (SEQ ID NO: 19) | tagcgtaaaaggagcaacatag (SEQ ID NO: 20) |
| RPL13A | cctggaggagaagaggaaaga (SEQ ID NO: 21) | ttgaggacctctgtgtatttg (SEQ ID NO: 22) |
| B2M | tgctgtctccatgtttgatgt (SEQ ID NO: 23) | tctctgctccccacctctaag (SEQ ID NO: 24) |
| EBNA1 | atcagggccaagacatagaga (SEQ ID NO: 25) | gccaatgcaacttggacgtt (SEQ ID NO: 26) |
| EBNA2 | catagaagaagaagaggatgaaga (SEQ ID NO: 27) | gtagggattcgagggaattactga (SEQ ID NO: 28) |
| LMP1 | atggaacacgaccttgaga (SEQ ID NO: 29) | tgagcaggatgaggtctagg (SEQ ID NO: 30) |
| BZLF1 | cacctcaacctggagacaat (SEQ ID NO: 31) | tgaagcaggcgtggtttcaa (SEQ ID NO: 32) |
| OriP | tcgggggtgttagagacaac (SEQ ID NO: 33) | ttccacgagggtagtgaacc (SEQ ID NO: 34) |
| GAPDH | accacagtccatgccatcac (SEQ ID NO: 35) | tccaccaccctgttgctgta (SEQ ID NO: 36) |
| TDGF | tccttctacggacggaactg (SEQ ID NO: 37) | agaaatgcctgaggaaagca (SEQ ID NO: 38) |
| NCAM1 | gattcctcctccaccctcac (SEQ ID NO: 39) | caatattctgcctggcctggatg (SEQ ID NO: 40) |
| HAND1 | ccacacccactcagagccatt (SEQ ID NO: 41) | caccccaccaccaaaaccttt (SEQ ID NO: 42) |
| MSX1 | cgagaggaccccgtggatgcagag (SEQ ID NO: 43) | ggcggccatcttcagcttctccag (SEQ ID NO: 44) |
| AFP | gaatgctgcaaactgaccacgctggaac (SEQ ID NO: 45) | tggcattcaagaggggttttcagtctgga (SEQ ID NO: 46) |
| SMN PCR-RFLP | ctatcatgctggctgcct (SEQ ID NO: 47) | ctacaacacccttctcacag (SEQ ID NO: 48) |

EXAMPLE 14

Cytogenetic Stability of PBMC Vs. Fibroblast-Derived iPSC Lines

TABLE 3A

Cytogenetic Stability of PBMCs BC-iPSCs

| Description | Numbers | % abnormal |
|---|---|---|
| Total iPSC lines | 90 | 3.3% |
| Total abnormal | 3 | |
| *Total with non-clonal aberration | 3 | 3.3% |

TABLE 3B

Cytogenetic Stability of PBMCs Fibroblast-iPSCs

| Description | Numbers | % abnormal |
|---|---|---|
| Total iPSC lines | 242 | 25.6% |
| Total abnormal | 62 | |
| *Total with non-clonal aberration | 17 | 7.0% |

EXAMPLE 15

Cytogenetic Stability of PBMC Vs. Fibroblast-Derived iPSC Lines Array CGH

TABLE 4A

Cytogenetic Stability of PBMCs BC-iPSCs

| Description | Numbers |
|---|---|
| Total iPSC lines | 7 |
| De Novo* amp/dels | 4 |

TABLE 4A-continued

Cytogenetic Stability of PBMCs BC-iPSCs

| Description | Numbers |
|---|---|
| Average De Novo amp/dels | 0.6 |
| De Novo amp/dels per passage | 0.036 |

TABLE 4B

Cytogenetic Stability of PBMCs Fibroblast-iPSCs

| Description | Numbers |
|---|---|
| Total iPSC lines | 6 |
| De Novo amp/dels | 19 |
| Average De Novo amp/dels | 3.2 |
| De Novo* amp/dels per passage | 0.136 |

A variety of results demonstrating superior properties of BC-iPSCs are shown, including specific cell lines. High Success rate of peripheral blood mononuclear cell (PBMC)-based episomal reprogramming on MEFs is shown in Table 5. Frequency of different types of karyotype abnormalities at individual; chromosomal level observed by G-band karyotyping in fibroblast-derived iPSCs. Rearr.—Rearrangement; Inv.—Inversion; Der.—derivatives is shown in Table 6. Success rate of blood-based reprogramming on human recombinant laminin 521 in defined E7 reprogramming media is shown in Table 7. Lack of success of blood-based episomal reprogramming on Matrigel substrate and defined E7 reprogramming media is shown in Table 8.

TABLE 5

High Success rate of peripheral blood mononuclear cell (PBMC)-based episomal reprogramming on MEFs.

| Line | Condition | Fresh/Frozen | Starting cell number | Plasmid | T - Total | T - Picked | Efficiency | Success rate | NT - Total | NT - Picked | Efficiency | Success rate |
|---|---|---|---|---|---|---|---|---|---|---|---|---|
| 02iCTR | MEFs/PESC | Fresh | 3.00E+06 | 4P | 22 | 22 | 7.33E−04 | 1 | 3 | 3 | 1.00E−06 | 1 |
| 03iCTR | MEFs/PESC | Fresh | 3.00E+06 | 4P | 9 | 9 | 3.00E−04 | 1 | 8 | 8 | 2.67E−06 | 1 |
| 03iCTR | MEFs/PESC | Cryopreserved | 5.00E+06 | 4P | 5 | 5 | 1.00E−04 | 1 | 0 | 0 | 0.00E+00 | 0 |
| 14isALS- | MEFs/PESC | Cryopreserved | 5.00E+06 | 5P | 21 | 21 | 4.20E−04 | 1 | 2 | 2 | 4.00E−07 | 1 |
| 80iCTR- #2 | MEFs/PESC | Cryopreserved | 5.00E+06 | 5P | 10 | 10 | 2.00E−04 | 1 | 0 | 0 | 0.00E+00 | 0 |
| 51iALS- | MEFs/PESC | Cryopreserved | 5.00E+06 | 5P | 12 | 8 | 2.40E−04 | 1 | 2 | 2 | 4.00E−07 | 1 |
| 89iALS- | MEFs/PESC | Cryopreserved | 5.00E+06 | 5P | 15 | 15 | 3.00E−04 | 1 | 14 | 14 | 2.80E−06 | 1 |
| 138iALS- | MEFs/PESC | Cryopreserved | 5.00E+06 | 5P | 5 | 5 | 1.00E−04 | 1 | 0 | 0 | 0.00E+00 | 0 |
| 152iALS | MEFs/PESC | Cryopreserved | 5.00E+06 | 5P | 7 | 7 | 1.40E−04 | 1 | 0 | 0 | 0.00E+00 | 0 |
| 07iASD | MEFs/PESC | Cryopreserved | 5.00E+06 | 5P | 18 | 18 | 3.60E−04 | 1 | 12 | 12 | 2.40E−06 | 1 |
| 53iALS-SOD1A4V | MEFs/PESC | Cryopreserved | 5.00E+06 | 5P | 9 | 8 | 1.80E−04 | 1 | 15 | 13 | 3.00E−06 | 1 |
| 134iALS-C9 | MEFs/PESC | Cryopreserved | 5.00E+06 | 5P | 8 | 8 | 1.60E−04 | 1 | 12 | 12 | 2.40E−06 | 1 |
| 58iALS-C9 | MEFs/PESC | Cryopreserved | 5.00E+06 | 5P | 4 | 4 | 8.00E−05 | 1 | 2 | 2 | 4.00E−07 | 1 |
| 37iALS-C9 | MEFs/PESC | Cryopreserved | 5.00E+06 | 5P | 0 | 0 | 0.00E+00 | 0 | NP | NP | | |
| 79iCTR | MEFs/PECS | Cryopreserved | 5.00E+06 | 5P | 0 | 0 | 0.00E+00 | 0 | NP | NP | | |
| 98iALS- | MEFs/PESC | Cryopreserved | 5.00E+06 | 5P | 6 | 6 | 1.20E−04 | 1 | 3 | 3 | 6.00E−07 | 1 |
| 700iCTR- | MEFs/PESC | Cryopreserved | 5.00E+06 | 5P | 12 | 12 | 2.40E−04 | 1 | 9 | 9 | 1.80E−06 | 1 |
| 012iASD | MEFs/PESC | Cryopreserved | 5.00E+06 | 5P | 12 | 12 | 2.40E−04 | 1 | 1 | 1 | 2.00E−07 | 1 |
| 776iCLN6 | MEFs/PESC | Cryopreserved | 5.00E+06 | 5P | 12 | 12 | 2.40E−04 | 1 | 5 | 5 | 1.00E−06 | 1 |
| 013iCTR | MEFs/PESC | Cryopreserved | 5.00E+06 | 5P | NP | NP | | | 12 | 12 | 2.40E−06 | 1 |
| 770iCLN6 | MEFs/PESC | Cryopreserved | 5.00E+06 | 5P | 12 | 12 | 2.40E−04 | 1 | 12 | 12 | 2.40E−06 | 1 |
| 013iCTR | MEFs/PESC | Cryopreserved | 5.00E+06 | 5P | NP | NP | | | 12 | 12 | 2.40E−06 | 1 |

TABLE 5-continued

High Success rate of peripheral blood mononuclear cell (PBMC)-based episomal reprogramming on MEFs.

| Line | Condition | Fresh/Frozen | Starting cell number | Plasmid | T - Total | T - Picked | Efficiency | Success rate | NT - Total | NT - Picked | Efficiency | Success rate |
|---|---|---|---|---|---|---|---|---|---|---|---|---|
| XH7iCTR | MEFs/PESC | Cryopreserved | 5.00E+06 | 5P | NP | NP | | | 12 | 12 | 2.40E-06 | 1 |
| WP3iCTR | MEFs/PESC | Cryopreserved | 5.00E+06 | 5P | NP | NP | | | 12 | 12 | 2.40E-06 | 1 |
| FP5iCTR | MEFs/PESC | Cryopreserved | 5.00E+06 | 5P | NP | NP | | | 1 | 1 | 2.00E-07 | 1 |
| 702iGAN | MEFs/PESC | Cryopreserved | 5.00E+06 | 5P | NP | NP | | | 12 | 12 | 2.40E-06 | 1 |
| 116iFNDI-nxx | MEFs/PESC | Cryopreserved | 5.00E+06 | 5P | NP | NP | | | 12 | 12 | 2.40E-06 | 1 |
| 361iGAN-nxx | MEFs/PESC | Cryopreserved | 5.00E+06 | 5P | NP | NP | | | 6 | 6 | 1.20E-06 | 1 |
| 012iGAN-nxx | MEFs/PESC | Cryopreserved | 5.00E+06 | 5P | NP | NP | | | 6 | 6 | 1.20E-06 | 1 |
| 2EVPiALS-nxx | MEFs/PESC | Cryopreserved | 5.00E+06 | 5P | NP | NP | | | 6 | 6 | 1.20E-06 | 1 |
| 7YXLiALS-nxx | MEFs/PESC | Cryopreserved | 5.00E+06 | 5P | NP | NP | | | 4 | 4 | 8.00E-07 | 1 |
| 9XXZiALS-nxx | MEFs/PESC | Cryopreserved | 5.00E+06 | 5P | NP | NP | | | 2 | 2 | 4.00E-07 | 1 |
| 6MBUiALS-nxx | MEFs/PESC | Cryopreserved | 5.00E+06 | 5P | NP | NP | | | 6 | 6 | 1.20E-06 | 1 |
| 5XVDiALS-nxx | MEFs/PESC | Cryopreserved | 5.00E+06 | 5P | NP | NP | | | 6 | 6 | 1.20E-06 | 1 |
| 7MTJiALS-nxx | MEFs/PESC | Cryopreserved | 5.00E+06 | 5P | NP | NP | | | 6 | 6 | 1.20E-06 | 1 |
| 0JGZiALS-nxx | MEFs/PESC | Cryopreserved | 5.00E+06 | 5P | NP | NP | | | 6 | 5 | 1.20E-06 | 1 |
| 9ZZ5iALS- | MEFs/PESC | Cryopreserved | 5.00E+06 | 5P | NP | NP | | | 6 | 6 | 1.20E-06 | 1 |
| 7AF6iALS- | MEFs/PESC | Cryopreserved | 5.00E+06 | 5P | NP | NP | | | 9 | 7 | 1.80E-06 | 1 |
| 2UNGiALS-nxx | MEFs/PESC | Cryopreserved | 5.00E+06 | 5P | NP | NP | | | 6 | 6 | 1.20E-06 | 1 |
| IDGFiALS-nxx | MEFs/PESC | Cryopreserved | 5.00E+06 | 5P | NP | NP | | | 7 | 7 | 1.40E-06 | 1 |
| 9GXDiALS-nxx | MEFs/PESC | Cryopreserved | 5.00E+06 | 5P | NP | NP | | | 6 | 6 | 1.20E-06 | 1 |
| 2FN3iALS-nxx | MEFs/PESC | Cryopreserved | 5.00E+06 | 5P | NP | NP | | | 6 | 6 | 1.20E-06 | 1 |
| 6PYDiALS-nxx | MEFs/PESC | Cryopreserved | 5.00E+06 | 5P | NP | NP | | | 6 | 6 | 1.20E-06 | 1 |
| Average | | | | | | | 2.20E-04 | 90.00% | | | 1.40E-04 | 90.24% |

NP: Not performed
T: T cell reprogramming method
NT: non-T cell reprogramming method
4P/5P: reprogramming factors on 4 or 5 plasmids

TABLE 6

Frequency of different types of karyotype abnormalitie

| | % Abnormalities | | | | | | Rank | | | |
|---|---|---|---|---|---|---|---|---|---|---|
| Chromosome | Total | Gain | Loss | Rearr. | Inv. | Der. | Total | Gain | Loss | Rearr. |
| chr1 | 11.8% | 15.8% | 0.0% | 13.9% | 0.0% | 0.0% | 2 | 2 | 8 | 1 |
| chr2 | 0.0% | 0.0% | 0.0% | 0.0% | 0.0% | 0.0% | 21 | 13 | 8 | 16 |
| chr3 | 4.9% | 5.3% | 7.7% | 2.8% | 0.0% | 0.0% | 9 | 6 | 3 | 11 |
| chr4 | 2.1% | 0.0% | 0.0% | 8.3% | 0.0% | 0.0% | 12 | 13 | 8 | 4 |
| chr5 | 0.0% | 0.0% | 0.0% | 0.0% | 0.0% | 0.0% | 21 | 13 | 8 | 16 |
| chr6 | 6.9% | 10.5% | 0.0% | 5.6% | 0.0% | 0.0% | 6 | 4 | 8 | 7 |
| chr7 | 0.0% | 0.0% | 0.0% | 0.0% | 0.0% | 0.0% | 21 | 13 | 8 | 16 |
| chr8 | 4.2% | 5.3% | 0.0% | 5.6% | 0.0% | 0.0% | 10 | 6 | 8 | 7 |
| chr9 | 2.1% | 0.0% | 0.0% | 8.3% | 0.0% | 0.0% | 12 | 13 | 8 | 4 |
| chr10 | 0.7% | 0.0% | 0.0% | 2.8% | 0.0% | 0.0% | 19 | 13 | 8 | 11 |
| chr11 | 6.9% | 13.2% | 0.0% | 0.0% | 0.0% | 0.0% | 6 | 3 | 8 | 16 |
| chr12 | 11.1% | 21.1% | 0.0% | 0.0% | 0.0% | 0.0% | 3 | 1 | 8 | 16 |
| chr13 | 13.2% | 7.9% | 7.7% | 13.9% | 100.0% | 100.0% | 1 | 5 | 3 | 1 |
| chr14 | 5.6% | 5.3% | 0.0% | 11.1% | 0.0% | 0.0% | 8 | 6 | 8 | 3 |
| chr15 | 3.5% | 2.6% | 7.7% | 2.8% | 0.0% | 0.0% | 11 | 11 | 3 | 11 |
| chr16 | 1.4% | 2.6% | 0.0% | 0.0% | 0.0% | 0.0% | 15 | 11 | 8 | 16 |
| chr17 | 1.4% | 0.0% | 7.7% | 0.0% | 0.0% | 0.0% | 15 | 13 | 3 | 16 |
| chr18 | 1.4% | 0.0% | 7.7% | 0.0% | 0.0% | 0.0% | 15 | 13 | 3 | 16 |
| chr19 | 1.4% | 0.0% | 0.0% | 5.6% | 0.0% | 0.0% | 15 | 13 | 8 | 7 |
| chr20 | 2.1% | 0.0% | 0.0% | 8.3% | 0.0% | 0.0% | 12 | 13 | 8 | 4 |
| chr21 | 8.3% | 5.3% | 23.1% | 5.6% | 0.0% | 0.0% | 5 | 6 | 2 | 7 |
| chr22 | 0.7% | 0.0% | 0.0% | 2.8% | 0.0% | 0.0% | 19 | 13 | 8 | 11 |
| chrX | 10.4% | 5.3% | 38.5% | 2.8% | 0.0% | 0.0% | 4 | 6 | 1 | 11 |

TABLE 7

Success rate of blood-based reprogramming on human recombinant laminin 521

| 02iCTR | MEFs/PESC | Fresh | 3.00E+06 | 4P | 22 | 22 | 7.33E-04 | 1 | 3 | 3 | 1.00E-06 | 1 |
|---|---|---|---|---|---|---|---|---|---|---|---|---|
| 02iCTR | L521/E7 | Fresh | 3.00E+06 | 4P | 3 | 3 | 1.00E-04 | 1 | 1 | 1 | 3.33E-05 | 1 |
| 03iCTR | L521/E7 | Cryopreserved | 5.00E+06 | 5P | 19 | 12 | 3.80E-04 | 1 | 34 | 12 | 6.80E-04 | 1 |
| 14isALS- | L521/E7 | Cryopreserved | 5.00E+06 | 4P | 0 | 0 | 0.00E+00 | 0 | 0 | 0 | 0.00E+00 | 0 |
| 80iCTR- | L521/E7 | Cryopreserved | 5.00E+06 | 5P | 4 | 4 | 8.00E-05 | 1 | 0 | 0 | 0.00E+00 | 0 |
| 80iCTR- #2 | L521/E7 | Cryopreserved | 5.00E+06 | 5P | NP | NP | NP | | 0 | 0 | 0.00E+00 | 0 |
| 89iALS- | L521/E7 | Cryopreserved | 5.00E+06 | 5P | 49 | 15 | 9.80E-04 | 1 | 0 | 0 | 0.00E+00 | 0 |

TABLE 7-continued

Success rate of blood-based reprogramming on human recombinant laminin 521

| | | | | | | | | | | | | | | |
|---|---|---|---|---|---|---|---|---|---|---|---|---|---|---|
| 138iALS- | L521/E7 | Cryopreserved | 5.00E+06 | 4P | 0 | 0 | 0.00E+00 | 0 | | 0 | 0 | 0.00E+00 | 0 | |
| 07iCTR- | L521/E7 | Cryopreserved | 5.00E+06 | 5P | 49 | 16 | 9.80E−04 | 1 | | 102 | 18 | 2.04E−03 | 1 | |
| 179iCTR- | L521/E7 | Cryopreserved | 5.00E+06 | 5P | NP | NP | NP | | | 1 | 1 | 2.00E−05 | 1 | |
| 201iCTR- | L521/E7 | Cryopreserved | 5.00E+06 | 5P | 6 | 6 | 1.20E−04 | 1 | | 4 | 4 | 8.00E−05 | 1 | |
| 202iCTR- | L521/E7 | Cryopreserved | 5.00E+06 | 5P | 0 | 0 | 0.00E+00 | 0 | | 4 | 4 | 8.00E−05 | 1 | |
| 206iCTR | L521/E7 | Cryopreserved | 5.00E+06 | 5P | 5 | 5 | 1.00E−04 | 1 | | NP | NP | NP | | |
| 166isALS | L521/E7 | Cryopreserved | 5.00E+06 | 5P | 5 | 5 | 1.00E−04 | 1 | | NP | NP | NP | | |
| 276iCTR | L521/E7 | Cryopreserved | 5.00E+06 | 5P | 12 | 12 | 2.40E−04 | 1 | | 36 | 12 | 7.20E−04 | 1 | |
| 6PYDiALS-nxx | L521/E7 | Cryopreserved | 5.00E+06 | 5P | NP | NP | NP | | | 6 | 6 | 1.20E−04 | 1 | |
| Average | | | | | | | 2.57E−04 | 75.00% | | | | 2.90E−04 | 61.54% | |

NP: Not performed
T: T cell reprogramming method
NT: non-T cell reprogramming method
4P/5P: reprogramming factors on 4 or 5 plasmids

TABLE 8

Relative lack of success of blood-based episomal reprogramming on Matrigel substrate

| | | | | | | | | | | | | | |
|---|---|---|---|---|---|---|---|---|---|---|---|---|---|
| CS02iCTR | MG/LCLRM | Fresh | 3.00E+06 | 4p | 0 | 0 | 0.00E+00 | 0 | 0 | 0 | 0.00E+00 | 0 | |
| CS03iCTR | MG/E7 | Frozen | 5.00E+06 | 4p | 0 | 0 | 0.00E+00 | 0 | 0 | 0 | 0.00E+00 | 0 | |
| 6PYDiALS | 2[MG]/E7 | Frozen | 5.00E+06 | 5p | NP | NP | | | 0 | 0 | 0.00E+00 | 0 | |
| Average | | | | | | | 2.57E−04 | 75.00% | | | 2.90E−04 | 61.54% | |

NP: Not performed
T: T cell reprogramming method
NT: non-T cell reprogramming method
4P/5P: reprogramming factors on 4 or 5 plasmids

EXAMPLE 16

PBMCs Isolated from a Blood Draw are Reliably Reprogrammed to iPSCs

Dermal fibroblasts obtained from a skin biopsy have been the most common source of iPSC reprogramming material, due largely to their inexpensive and relatively easy usage. However, compared to a blood draw, a skin punch biopsy can be between the size of 3-4 mm and is often a painful procedure that requires local anesthetics. Compared to skin biopsy-derived fibroblasts, blood is a more accessible source of patient tissue during hospital visits and, therefore, a preferred choice of source tissue for iPSC reprogramming by both patients and clinicians. Various human blood reprogramming methods have been reported with mixed efficiencies, including CD34$^+$ cells mobilized from peripheral blood (ref). Unless isolated from cord blood, CD34$^+$ cells are usually isolated from the peripheral blood or bone marrow of patients undergoing G-CSF mobilization for several days. In order to generate sufficient cell numbers for reprogramming, isolated CD34$^+$ progenitor cells need to be enriched and expanded in culture with complex and expensive protocols. The Inventors were successful in reprogramming PBMCs that were freshly isolated from a peripheral blood draw without prior cell expansion or CD34$^+$ cell isolation using episomal reprogramming plasmids. Such an approach provides the fastest and most cost effective procedure for obtaining a patient's reprogrammed iPSCs from the time of collecting a patient bio-specimen to generating their rigorously characterized iPSCs.

Reprogramming large cohorts of PBMCs from multiple subjects simultaneously as well as iPSC line generation at a much later date after a patient blood draw that allows for iPSC "future-proofing", requires a PBMC cryopreservation step to recover viable cells reliably. Additionally, this process is flexible because selective cohorts of well cryopreserved PBMCs from representative patients could be converted to iPSCs when greater patient genotype-phenotype information is available. However, when cryopreserved PBMCs from multiple individuals were reprogrammed to iPSCs with episomal plasmids expressing POU5F1, SOX2, KLF4, LIN28, L-MYC, p53 shRNA, the Inventors observed significant variability in isolating identifiable iPSC clones even after 35-40 days, regardless of PBMC cell type, ECM substrata and media). The T reprogramming method was successful with only 33% of PBMC samples, while the non-T method on cryopreserved PBMCs did not result in any clonal iPSC lines (data not shown).

Critically, the reliability of PBMC reprogramming in our hands was improved significantly when the Inventors utilized, (a) two additional episomal plasmids containing SV40 large T antigen (SV40LT) and EBNA-1 in specific stoichiometry to minimize PBMC cell death and sustain reprogramming factor plasmid expression and (b) a defined reprogramming media to promote high surface attachment of the nucleofected PBMCs (FIG. 8A). This novel protocol resulted in successful and efficient generation of multiple adherent PBMC-iPSC clones that could be mechanically isolated and scaled up for expansion after 25-35 days post-nucleofection (FIG. 8A). Importantly, the success rate in reprogramming multiple individual cryopreserved PBMCs from unaffected controls or diseased patients' was 90% for the T cell method and 83% for the non-T cell method (Table 5) on mouse embryonic fibroblast feeders (MEFs). Given the limitations imposed by T cell-iPSCs and the low efficiencies for PBMC-derived non-T cell reprogramming, this method resulted in reliable reprogramming of non-T cell derived BC-iPSCs.

Figures 11, 11A:
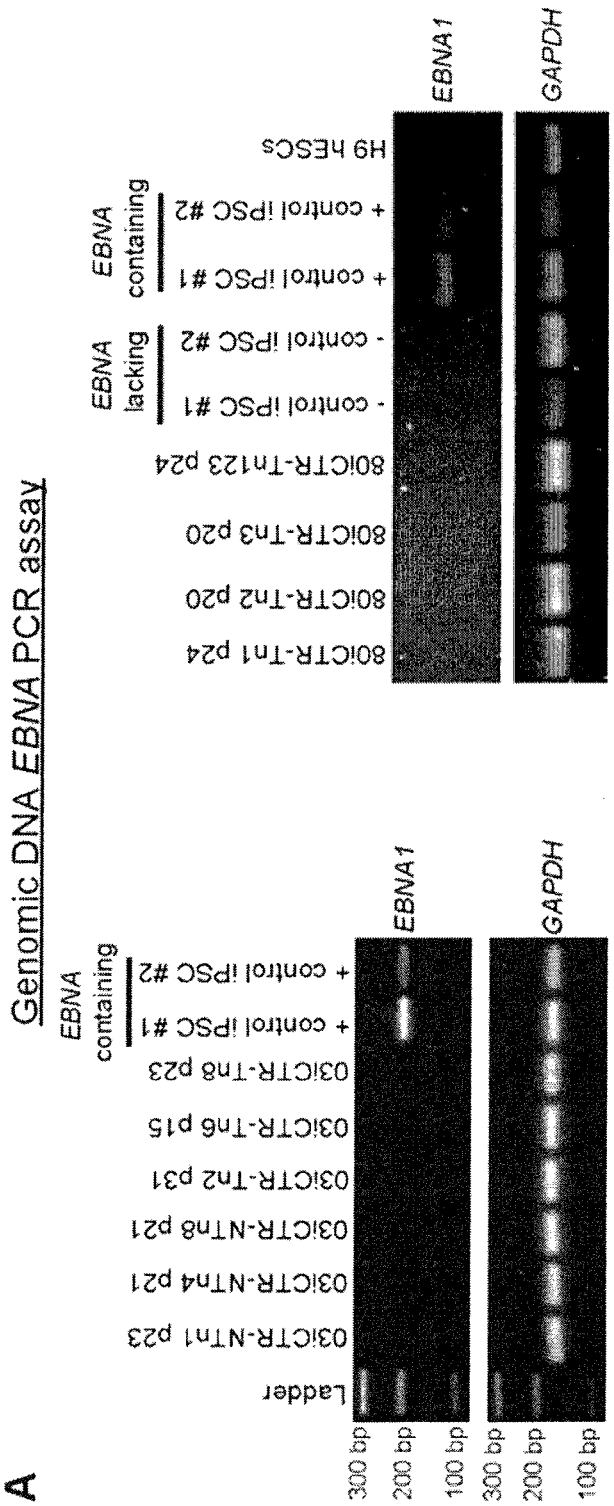
FIG. 11(A) to FIG. 11(C): Transgene-free status of BC-iPSCs.
FIG. 11 (B): Relative normalized gene expression measured by quantitative RT-PCR analyses using primers detecting endogenous POU5F1 (OCT4), SOX2, LIN28, L-MYC, and KLF4 expression (coding DNA sequence, CDS).
Figures 11, 11B:
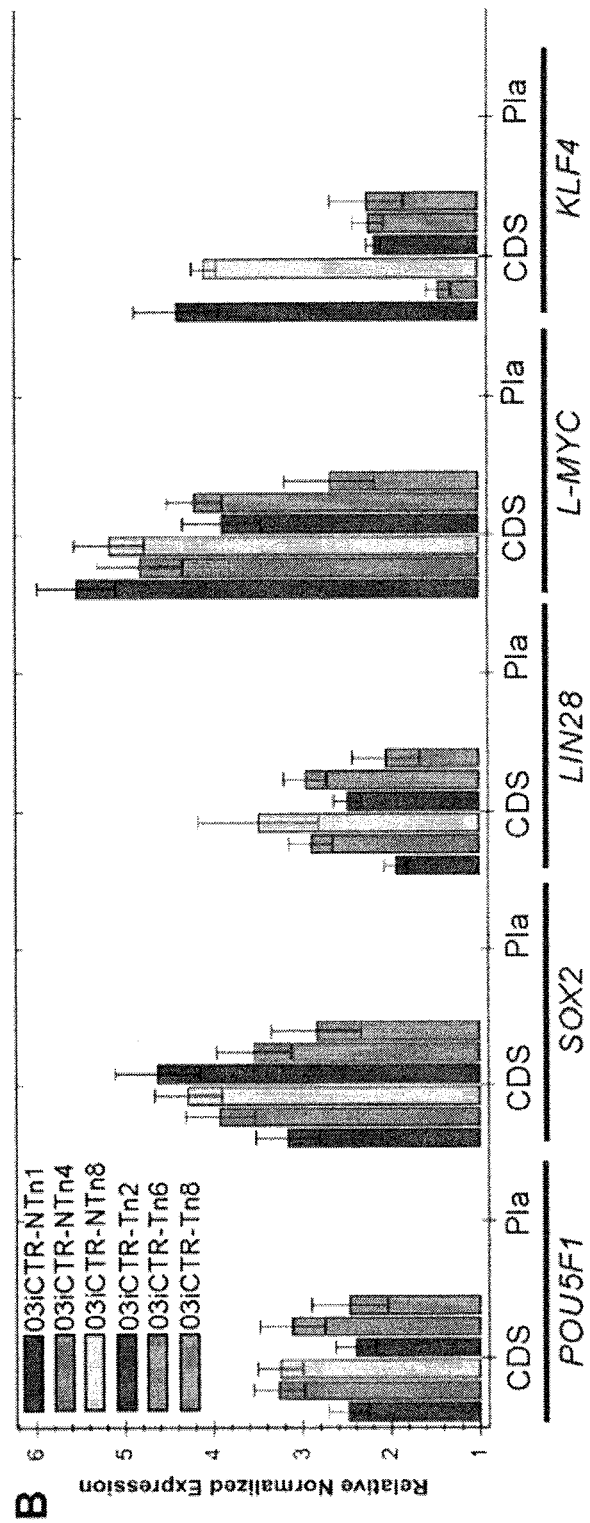
Figures 11, 11C:
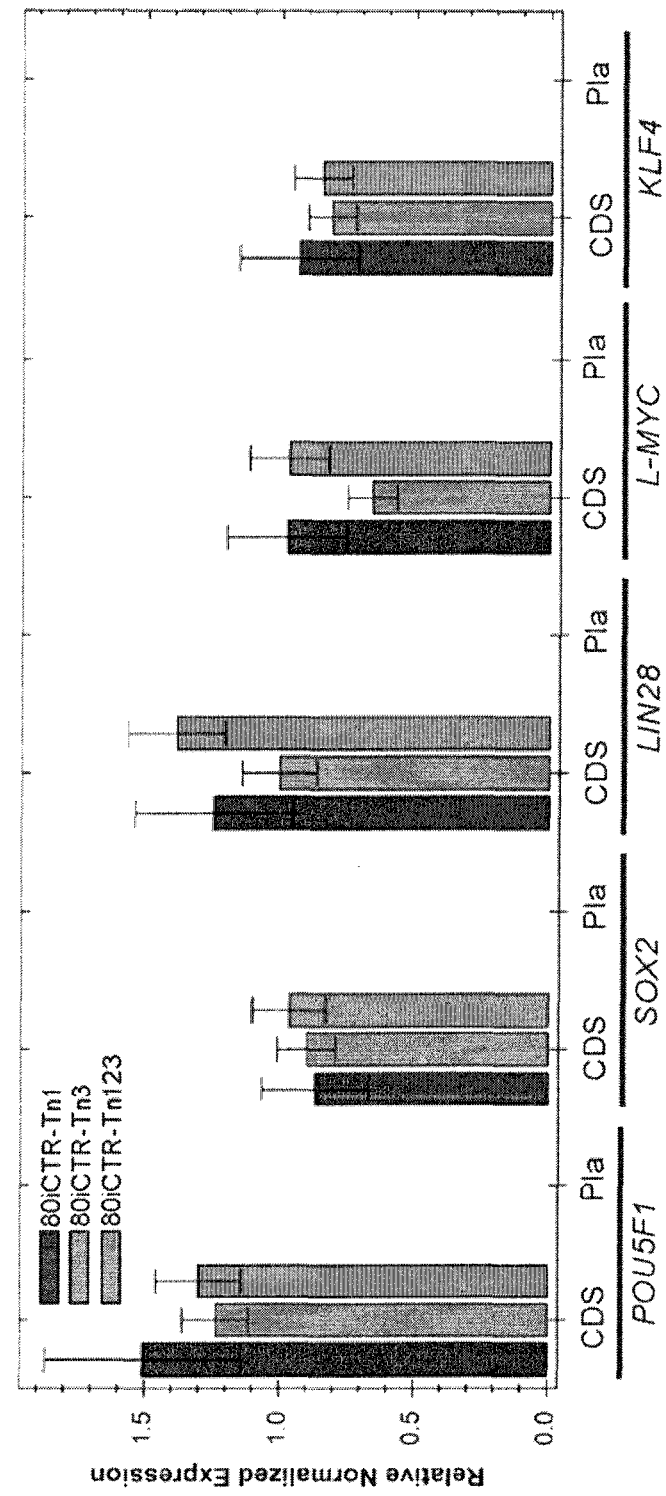

The Inventors next tested whether this new protocol was also amenable when using reprogramming methods that are more clinically compatible. Use of recombinant human laminin 521 substrate and chemically defined reprogramming media resulted in successful PBMC-reprogramming, albeit at a slightly lower success rate at 75% and 58%, respectively. The average reprogramming efficiency for T-cell and non-T cell method was $2.2\times10^{-4}$% and $1.6\times10^{-6}$%, respectively (Table 5). All the PBMC-iPSC lines exhibited typical PSC characteristics, including tightly packed colonies, high cell nuclear-cytoplasmic ratio, robust alkaline phosphatase activity, and expression of pluripotency antigens (FIG. 8B). The BC-iPSCs passed pluripotency quality control metrics determined by the PluriTest assay, demonstrating that the PBMC-iPSC transcription profile was analogous to well established hESCs and fib-iPSCs, but not differentiated fibroblasts and neural progenitor cells (FIG. 8C). BC-iPSCs maintained a normal G-band karyotype (FIG. 8D) and were confirmed to be clonal derivatives of either T cells or non-T cells from the PBMCs using the T cell receptor (TCR)-β and may, gene rearrangement/clonality assays (FIG. 8E). The trilineage potential of BC-iPSCs was demonstrated by spontaneous embryoid body formation and by measuring germ-layer specific gene expression profile by the TaqMan Scorecard assay (FIG. 8F). The "footprint-free" status of BC-iPSCs was confirmed by demonstration of endogenous pluripotency gene expression and absence of exogenous reprogramming transgenes using RT-qPCR (FIG. 11A). The EBNA plasmid-related latency element was eventually eliminated from the established BC-iPSCs (FIG. 11B).

EXAMPLE 17

BC-iPSCs have Equivalent Neuronal Differentiation Compared to Fib-iPSCs

It has been reported that iPSCs, regardless of the source tissue, ultimately lose most of their gene expression and epigenetic profiles related to the original cell source. However, it remains unclear whether blood-derived iPSCs can differentiate as efficiently as fibroblast-derived iPSCs into other various cell types, possibly due to a stronger retention of epigenetic memory in blood-sourced iPSCs. The Inventors addressed this by directing blood or fibroblast-derived iPSCs, both of mesodermal origin, to a different germ layer such as ectoderm. Specifically, the Inventors performed neural ectoderm differentiation from large numbers of fibroblast (n=26) and PBMC lines (n=8), from both healthy volunteers as well as diseased patients. Based on immunocytochemistry for neural ectoderm markers of TUBB3 ($\beta_3$-tubulin) and NKX6.1 and subsequent cell counts, neuronal differentiation was shown to occur at a similar efficiency between fibroblast and BC-iPSCs (FIG. 8G), further demonstrating the utility of BC-iPSCs.

EXAMPLE 18

BC-iPSCs Maintain a Significantly More Stable Karyotype Compared to Fib-iPSCs

Recurrent chromosomal abnormalities have been described previously for an abundant number of hESC lines. A few reports have chronicled common chromosomal aberrations for hiPSC lines, however, these did not methodically account for variability in source tissues, reprogramming methods and cell culture methods. To our knowledge, there have been no systematic studies describing cytogenetic analysis comparing frequency between iPSCs derived from fibroblast and blood. Over the past six years the Inventors performed routine cytogenetic analysis on iPSC lines derived from 104 unique fibroblast or PBMC donors, which includes 339 independent clonal iPSC lines. All fibroblast and blood-derived iPSCs assessed were reprogrammed using the similar non-integrating episomal reprogramming and standard feeder-free matrigel/mTeSR cell culture methods.

Although fib-iPSCs and BC-iPSCs derived in the iPSC Core resemble each other with regard to their reprogramming methods, pluripotency and differentiation, an early observation of striking differences in cytogenetic stability between the two source cell types prompted the need for large-scale comparative analyses. Many laboratories and stem cell repositories perform routine quality control assays of cytogenetic changes in PSCs using G-band karyotyping by obtaining cell metaphases and Giemsa staining of the chromosomes. This method can readily identify small subpopulations of abnormal cells where reliable identification of 5% abnormal cells is readily achieved, thus allowing detection of mosaicism (>10%) and balanced translocations at low resolution (>5-10 Mb).

Figures 6, 6A:
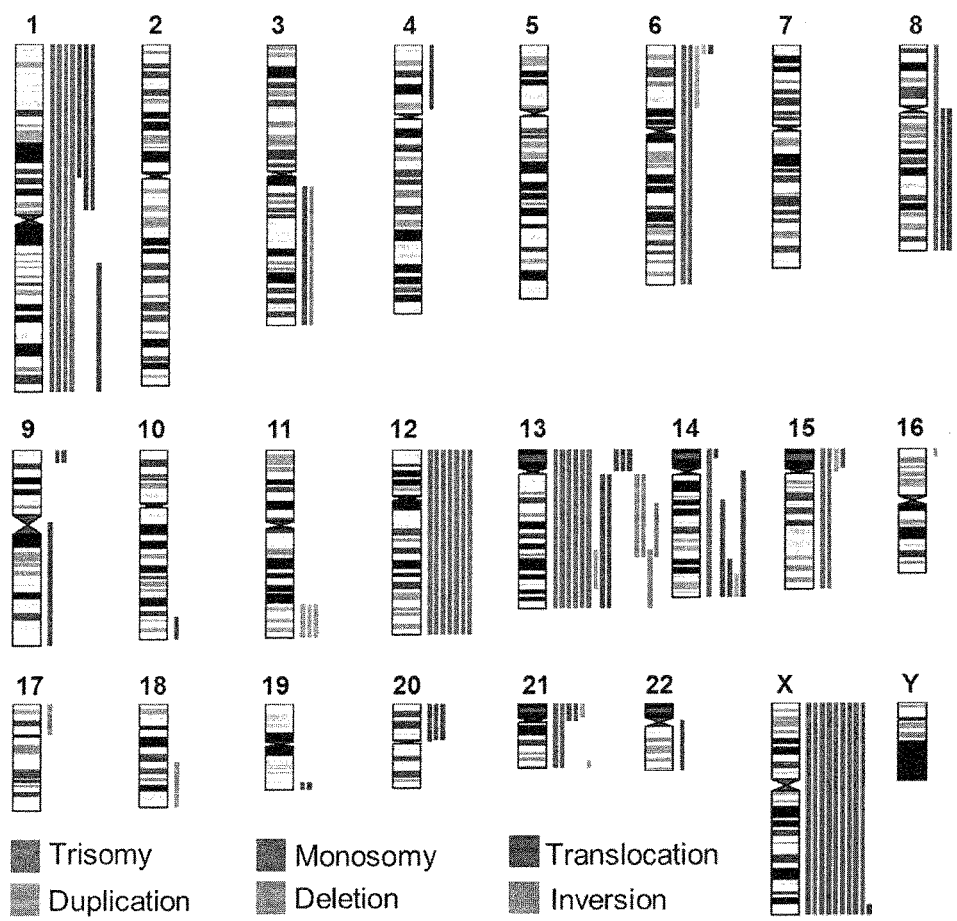
FIG. 6(A) to FIG. 6(B). Ideogram demonstrating the chromosomal changes observed in the iPSC lines are Cedars-Sinai iPSC Core. Each colored bar represents one chromosome change occurrence in one cell line. The cytogenetic changes are color coded; Marooon, monosomy, loss of a whole chromosome. BC-iPSCs are superior at maintaining stable karyotypes than fibroblast-derived iPSCs. Individual chromosome level ideogram representation of abnormal karyotypes from fibroblast-(FIG. 6(A)) and PBMC-derived iPSCs (FIG. 6(B)) in our laboratory. Abnormal iPSC karyotypes represented in the ideograms are.
Figures 6, 6B:
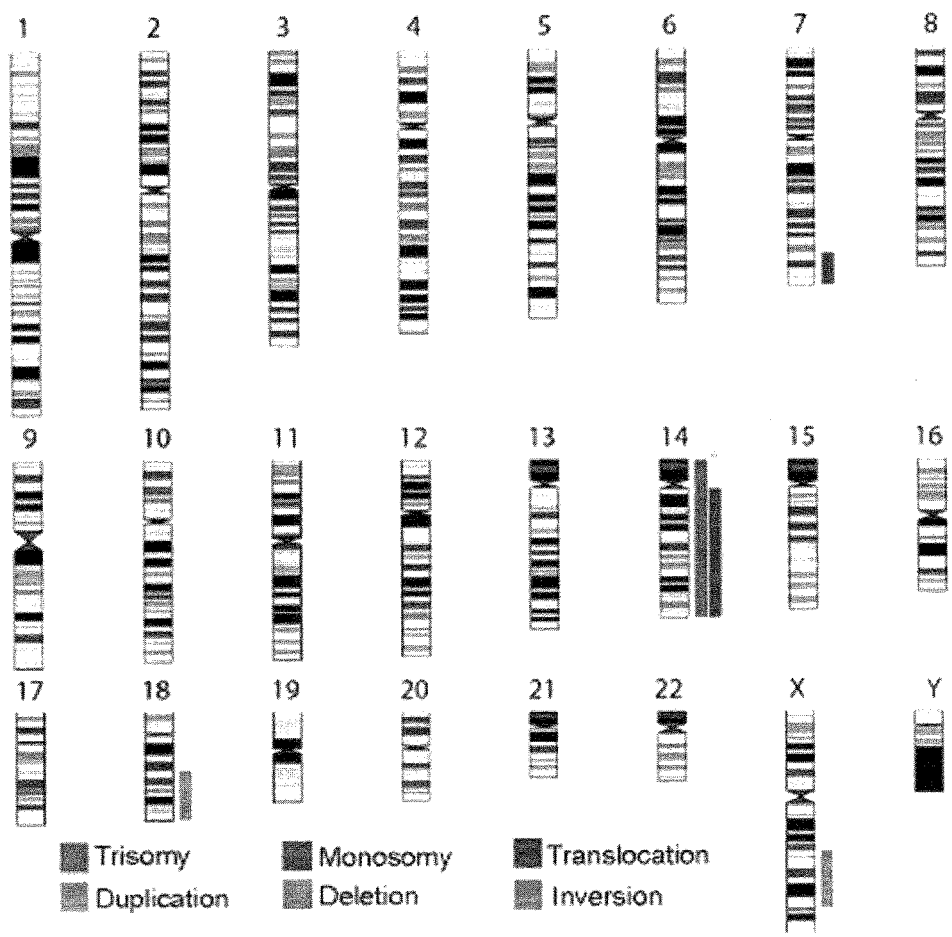
Figures 7, 7A:
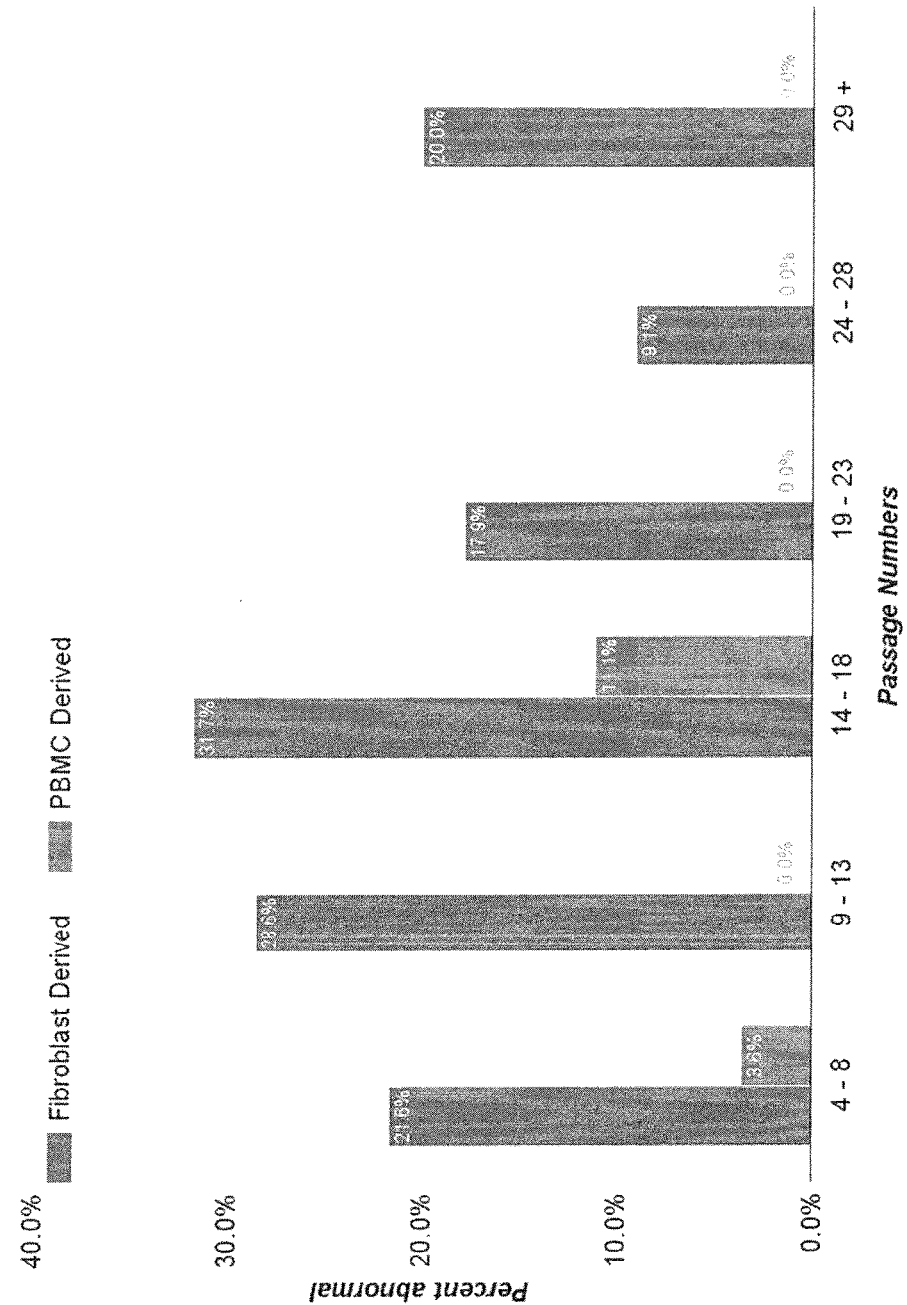
FIG. 7(A) to 7(B). Karyotypes.
Figures 7, 7B:
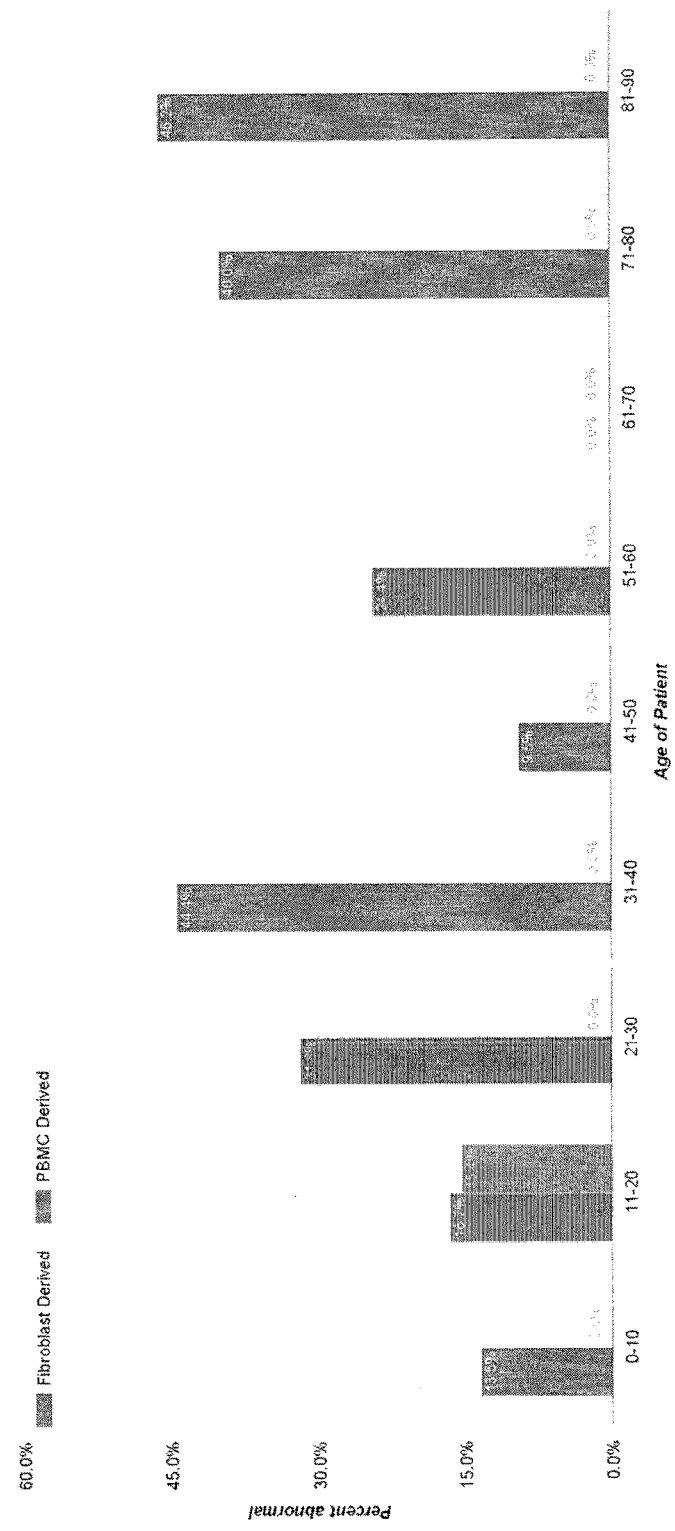
Figures 12, 12A:
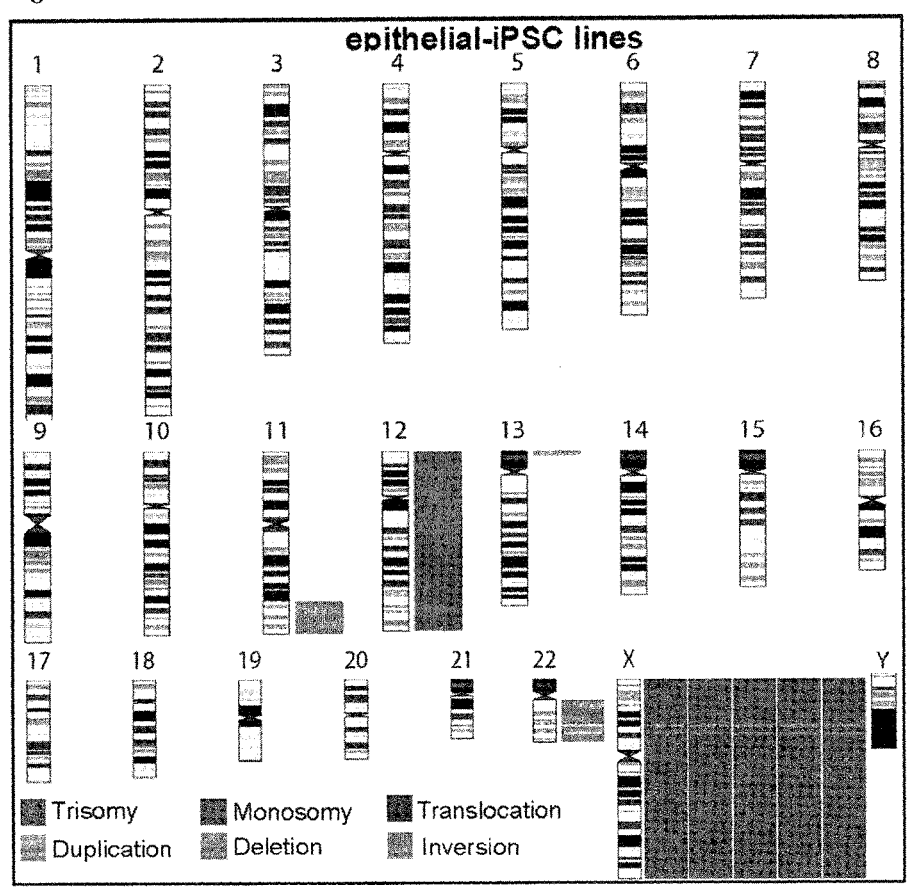
FIG. 12(A) to FIG. 12(B): Chromosomal ideograms of lymphoblastoid cell line (LCL)-iPSCs and epithelial cell-derived iPSCs. Individual chromosome level ideogram representation of abnormal karyotypes from LCL-derived FIG. 12(A) and epithelial-derived iPSCs FIG. 12(B) in our laboratory. Abnormal iPSC karyotypes represented in the ideograms are.
Figures 12, 12B:
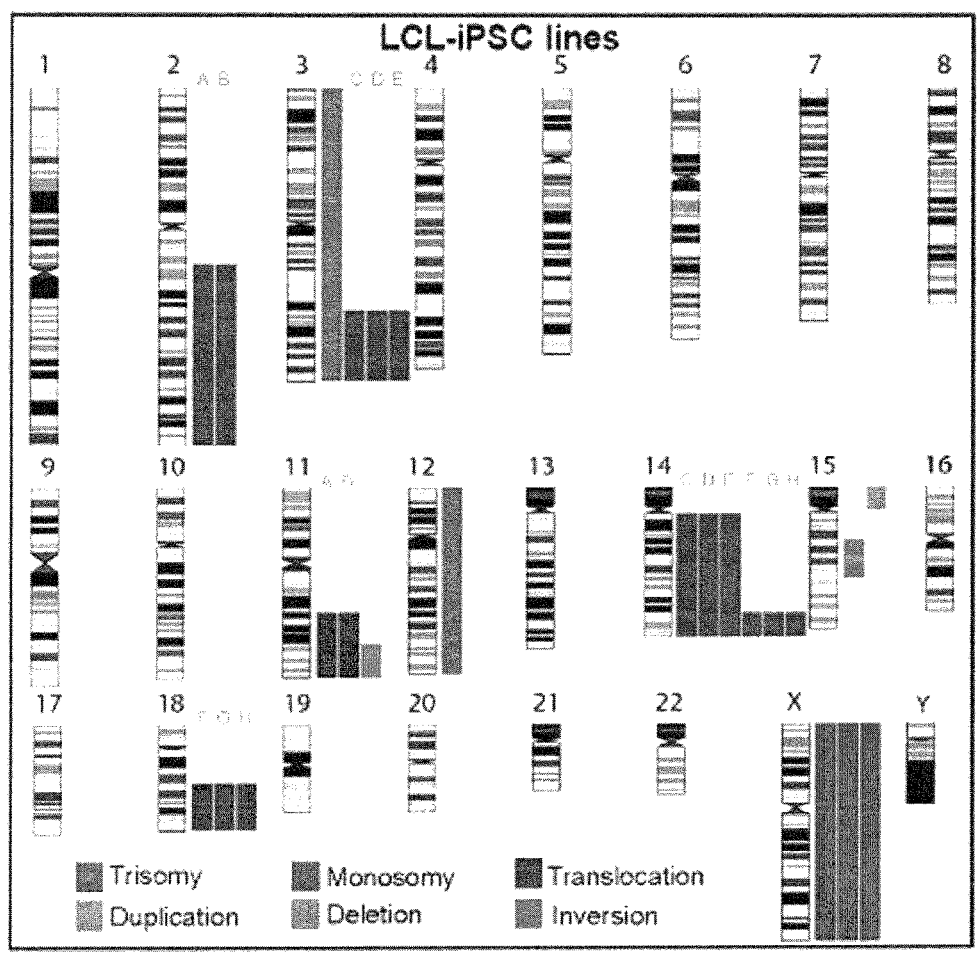

The Inventors performed karyotype analysis on 364 human iPSC cultures where source fibroblasts and PBMCs were collected from multiple laboratories or public repositories. Our data reveal remarkable differences in the incidence of chromosomal aberrations in fib-iPSCs and BC-iPSCs. Abnormal karyotypes with clonal aberrations were observed in 59 of 258 (22.9%) cultures from clonally independent human fib-iPSC lines, derived from 78 unique donors (FIG. 6). In stark contrast, only 4 in 106 (3.8%) cultures of clonal human PBMC-iPSC lines derived from 32 unique donors displayed low-frequency abnormalities. It is evident from the ideograms, schematic representation of the chromosomes, that recurrent aberrations are represented in much greater degree in in fib-iPSCs compared to the BC-iPSCs (FIG. 6). Indeed, this remarkable cytogenetic stability is unique to PBMCs, as iPSCs reprogrammed from other cell origins, including lymphoblastoid cell lines (25%) and primary epithelial cells (27%) have similar high rates of karyotypes aberrations (FIG. 12).

The most frequent karyotypic abnormalities in fib-iPSCs were observed in chromosomes 13 (13.2%), 1 (11.8%), 12 (11.1%), and X (10.4%) (Table 6). To a lesser extent karyotype changes were also observed in chromosomes 21, 11, and 6, in descending order of frequency. Of the aneuploidies, chromosomal gains (trisomy or duplications) were most commonly observed in 12 (21.1%), 1 (15.8%), 11 (13.2%), and 6 (10.5%) and chromosomal losses were repeatedly observed in chromosomes X (38.5%) and 21 (23.1%). Translocation rearrangements in chromosomes 1 and 13 (13.9%) and 14 (11.1%) in fib-iPSCs were also observed. BC-iPSCs had one line each display chromosome gains in 14 (trisomy) or 18 (duplication). The other two PBMC-iPSC lines had exhibited uncommon abnormalities: a translocation 46,XY,t(7;14)(q34;q11.2) and a mosaic deletion 46,X,del(X)(q22q26) in 19% of cells (Table 6).

EXAMPLE 19

Fib- and BC-iPSCs Karyotype Distribution Relates not to the Donor Age but Rather to Passage Number The skin, unlike the blood, is routinely exposed to external environmental elements like potential sun damage and the fibroblasts derived from the biopsies require a certain level of expansion prior to reprogramming, which is akin to further aging in culture. Given this, the Inventors posited that the donor age might be a contributing factor that impacts the cytogenetic instability of fib-iPSCs. However, with respect to the frequency of cytogenetic abnormalities in fib-iPSCs, the Inventors did not observe a significant trend or correlation with the age of the donor (FIG. 9A). Indeed, based on G band karyotype analysis, the highest percent of karyotype abnormalities (31.9%) was observed in the 21-40 age group fibroblast-iPSCs.

Pluripotent stem cells have a highly proliferative nature. As such, the Inventors next attempted to analyze how the fib- and BC-iPSCs fared over time in cell culture and whether increasing passage number led to a greater propensity for accumulating cytogenetic aberrations. About 21.6% of fibroblast-derived iPSCs were observed to have abnormal karyotypes (>1/20 cells with clonal aberrations) in their first G-band karyotype evaluation post-iPSC generation, which was typically between passages 4-23. In stark contrast, only 2.8% of BC-iPSCs had abnormal karyotypes in their first assessment. Any iPSC line that was determined to have an abnormal karyotype was no longer cultured or evaluated. Therefore, between $2^{nd}$ and $4^{th}$ repeat karyotypes were only evaluated on iPSC lines that were initially identified as cytogenetically normal in their first karyotype. This analysis allowed us to determine whether fib-iPSCs have an inherent level of cytogenetic instability over BC-iPSCs upon continued time in culture and passaging even after being established as normal post-iPSC generation (at their first G-band karyotype evaluation). G-band karyotyping showed that a greater proportion of fib-iPSCs (27.8%) acquired abnormal karyotypes in culture upon repeat karyotyping when compared to the proportion at first karyotypes ($P<0.001$, two way ANOVA with Bonferroni posttest), while the percent abnormal karyotypes in BC-iPSCs did not show any significant difference between first and repeat karyotypes (FIG. 9B). Upon analyzing the origin of the cytogenetic instability in fib-iPSCs, it appeared that the highest rate of abnormal karyotypes (first or repeat) occur during passages 10-23 in the life of the iPSC line (FIG. 9C-D), which is typically when the largest amount of iPSC expansion occurs for any given cell line. The iPSC expansion increases at passages 10-23 largely due to characterization and cell banking coinciding around these passage numbers. Nevertheless, this is a similar process for both fib- or BC-iPSCs, and yet the PBMC-derived cells do not display an increased disposition towards abnormal karyotypes upon extended culture or expansion.

EXAMPLE 20

BC-iPSCs Acquire Less Submicroscopic Amplifications and Deletions

G-band karyotype has the advantage that it can detect balanced translocations, inversions, <20% culture mosaicism, chromosomal position of genomic gains or losses as commonly observed in the fib-iPSC cultures (FIG. 6 and Table 5). However, since G-band karyotype is unable to detect submicroscopic genomic abnormalities (<5 Mb), the Inventors decided to conduct comparative genomic hybridization (aCGH) microarray on a subset of fib-iPSC and PBMC-iPSC lines. While aCGH is unable to detect balanced translocations, inversions and <20% culture mosaicism, it is a good supportive method to detect smaller size genomic gains and losses, copy number variants (CNVs), duplications/deletions, and unbalanced translocations in the iPSC lines. The Inventors analyzed and recorded any de novo amplifications or deletions acquired in the iPSCs upon comparison with the parental fibroblast or PBMC source bio-specimen. In this analysis only those amplifications and deletions acquired de novo in iPSCs were considered, when they were not normal CNVs upon cross referencing against the Database of Genomic Variants (DGV) that contains genomic variations observed in healthy individuals. Including iPSC lines with abnormal and normal G-band karyotypes, the average size of the amplification and deletions detected by aCGH were significantly greater in fib-iPSC lines at 44 Mb compared to 2.1 Mb in PBMC-iPSC lines (FIG. 10A), the preponderance of which was due to fib-iPSC lines with an abnormal karyotype (FIG. 10B). Upon segregating the size analysis comparison between iPSC lines with normal karyotypes, the de novo amps/dels were on average 2.31 Mb in fib-iPSCs and 2 Mb in PBMC-iPSC lines. Supporting this data, the average number of acquired de novo total amps/dels in fib-iPSCs (3.7) were at least twofold greater than in BC-iPSCs (1.8). Even in iPSC lines that were determined to have normal G-band karyotypes, the number of new amps/dels were greater in fib-iPSCs at 3.3 vs. BC-iPSCs at 1.8. The most commonly acquired submicroscopic (0.8-1.5 Mb) de novo amplifications or deletions in fib- or PBMC-iPSC lines detected by aCGH was amplification of chromosome 7q31.32 or deletion of chromosomes 10q15.2-q25.1, 16p11.2, 21p11.2-p11.1 (FIG. 10E).

Here the Inventors report a new and more reliable method for reprogramming of the non-T cell component of blood using episomal plasmids expressing pluripotency factors. Using the described reprogramming protocol, one is able to consistently reprogram non-T cells with close to 100% success from non-T cell or non-B cell sources. Further advantages include use of a defined reprogramming media E7 and using defined clinically compatible substrate recombinant human L-521. Blood cell-derived iPSCs ("BC-iPSCs") exhibited identical characteristics to fibroblastderived iPSCs ("fib-iPSCs"), retain genotype, exhibit a normal pluripotency profile, and readily differentiate into all three germlayer cell types. This method for reliably deriving iPSCs from patient blood samples paves the way for rapidly generate new human iPSC lines, including patient-specific lines, thus providing an enormous bioresource for disease modeling, drug discovery, and regenerative medicine applications.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of blood cells, cellular components of blood, pluripotent stem cells derived from therein, techniques and composition related to deriving pluripotent stem cells from blood cells cells, differentiating techniques and compositions, biomarkers associated with such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating blood cell derived induced pluripotent stem cells, comprising:
   providing a quantity of peripheral blood cells;
   fractioning the quantity of peripheral blood cells;
   isolating a layer of peripheral blood mononuclear cells from the fractionated peripheral blood cells;
   delivering a quantity of EBNA1 and reprogramming factors comprising Oct-4, Sox-2, Klf-4, 1-Myc, Lin-28, SV40 Large T Antigen ("SV40LT"), and short hairpin RNAs targeting p53 ("shRNA-p53") into the peripheral blood mononuclear cells; and
   culturing the peripheral blood mononuclear cells in a reprogramming media for at least 4 days, wherein delivering the EBNA1 and reprogramming factors, and culturing in a reprogramming media generates blood cell derived induced pluripotent stem cells, wherein the reprogramming factors are encoded in four oriP/EBNA1 derived vectors comprising:
   a first vector encoding Oct4, Sox2, SV4OLT and Klf4,
   a second vector encoding Oct4 and shRNA-p53,
   a third vector encoding Sox2 and Klf4, and
   a fourth vector encoding 1-Myc and Lin-28; and
   wherein a fifth oriP/EBNA1 vector encodes EBNA1.

2. The method of claim 1, wherein delivering a quantity of reprogramming factors comprises nucleofection.

3. The method of claim 1, wherein the five oriP/EBNA1 derived vectors are: pEP4 E02S ET2K, pCXLE-hOCT3/4-shp53-F, pCXLE-hSK, pCXLE-hUL, and pCXWB-EBNA1.

4. The method of claim 1, comprising plating of the peripheral mononuclear blood cells on a treated cell culture surface after delivering reprogramming factors into the blood cells, and culturing the blood cells in a reprogramming media on said treated cell culture surface.

5. The method of claim 4, wherein the treated cell culture surface comprises plating of mouse embryonic feeders (MEFs).

6. The method of claim 4, wherein the treated cell culture surface comprises an extracellular matrix protein.

7. The method of claim 6, wherein the extracellular matrix protein comprises laminin.

8. The method of claim 7, wherein laminin comprises L-521.

9. The method of claim 1, wherein the reprogramming media comprises media suitable for culturing of embryonic stem cells (ESCs).

10. The method of claim 9, wherein the media comprises basic fibroblast growth factor (bFGF).

11. The method of claim 1, wherein the reprogramming media comprises E7 media.

12. The method of claim 11, wherein the reprogramming media comprises E7 media comprising L-Ascorbic Acid, Transferrin, Sodium Bicarbonate, Insulin, Sodium Selenite and/or bFGF.

13. The method of claim 1, wherein culturing the peripheral mononuclear blood cells in a reprogramming media is for at least 4, 5, 6, 7, 8, 9, 10, 11, 12, 13, 14, 15, or 16 days.

14. The method of claim 1, wherein culturing the peripheral mononuclear blood cells in a reprogramming media is for at least 17, 18, 19, 20, 21, 22, 23, 24, 25, 26, 27, 28, 29, 30 or 31 days.

15. The method of claim 1, wherein the peripheral blood cells are isolated from a subject possessing a disease mutation.

16. The method of claim 15, wherein the disease mutation is associated with a neurodegenerative disease, disorder and/or condition.

17. The method of claim 15, wherein the disease mutation is associated with an inflammatory bowel disease, disorder, and/or condition.

18. The method of claim 1, wherein the peripheral blood cells are a sample drawn from a human subject.

19. The method of claim 3, wherein, the method comprises delivering 0.5 to 1.0 ug pCXLE-hOCT3/4-shp53, 0.5 to 1.0 ug pCXLE-hSK, 0.5 to 1.0 ug pCXLE-UL, 0.25 to 0.75 ug pCXWB-EBNA1 and 0.5 to 1.0 ug pEP4 E02S ET2K to 2 to $4\times10^6$ peripheral blood mononuclear cells.

20. The method of claim 3, wherein, the method comprises 0.83 ug pCXLE-hOCT3/4-shp53, 0.83 ug pCXLE-hSK, 0.83 ug pCXLE-UL, 0.5 ug pCXWB-EBNA1 and 0.83 ug pEP4 E02S ET2K and $3\times10^6$ peripheral blood mononuclear cells.

21. The method of claim 1, wherein the isolated peripheral blood cells comprise mononuclear cells substantially free of T-cells and B-cells.

* * * * *